United States Patent [19]

Pappas-Fader et al.

[11] Patent Number: 5,736,486

[45] Date of Patent: Apr. 7, 1998

US005736486A

[54] HERBICIDAL MIXTURE OF ANILOFOS AND PROPANIL

[75] Inventors: Thalia Pappas-Fader, Landenberg, Pa.; Daniel Carl Leep, Newark; Marc Ruggiero, Wilmington, both of Del.; William Francis Smith, III, Elkton, Md.; Alexander Yung-Shing Yang, Newark, Del.

[73] Assignee: E. I. du Pont de Nemours and Company, Wilmington, Del.

[21] Appl. No.: 549,107

[22] Filed: Oct. 27, 1995

Related U.S. Application Data

[60] Provisional application No. 60/002,049, Aug. 8, 1995, provisional application No. 60/001,448, Jul. 26, 1995, provisional application No. 60/001,272, Jul. 20, 1995, and provisional application No. 60/000,231, Jun. 15, 1995.

Related U.S. Application Data

[63] Continuation-in-part of Ser. No. 412,396, Mar. 28, 1995, abandoned, which is a continuation-in-part of Ser. No. 334,720, Nov. 4, 1994, abandoned.

[51] Int. Cl.$^6$ ............... A01N 37/22; A01N 57/06

[52] U.S. Cl. .................................................. 504/127
[58] Field of Search .................................. 504/127

[56] References Cited

U.S. PATENT DOCUMENTS

| | | |
|---|---|---|
| 4,278,461 | 7/1981 | Salbeck et al. . |
| 5,229,356 | 7/1993 | Tocker .................... 504/214 |
| 5,356,862 | 10/1994 | Zimmerman .................. 504/215 |

FOREIGN PATENT DOCUMENTS

| | | | |
|---|---|---|---|
| 4 236 475 | 6/1994 | Germany ............ A01N 57/14 |

*Primary Examiner*—S. Mark Clardy

[57] ABSTRACT

This invention relates to herbicidal mixtures of anilofos with propanil, or one or more of the compounds selected from azimsulfuron, metsulfuron methyl, chlorimuron ethyl, bensulfuron methyl, ethametsulfuron methyl, nicosulfuron, rimsulfuron, sulfometuron methyl, thifensulfuron methyl, tribenuron methyl, triflusulfuron methyl, methyl 2-[[[[(4,6-dimethoxy-2-pyrimidinyl)amino]carbonyl]amino]sulfonyl]-6-(trifluoro-methyl)-3-pyridinecarboxylate, chlorsulfuron, and hexazinone, herbicidal compositions of said mixtures, and a method for the use of said mixtures to control undesired vegetation.

4 Claims, No Drawings

HERBICIDAL MIXTURE OF ANILOFOS AND PROPANIL

CROSS REFERENCE TO RELATED APPLICATIONS

This is a continuation-in-part application which claims the benefit of U.S. Provisional application Ser. No. 60/002,049 filed Aug. 8, 1995; U.S. Provisional application Ser. No. 60/001,448 filed Jul. 26, 1995; U.S. Provisional application Ser. No. 60/001,272 filed Jul. 20, 1995; U.S. Provisional application Ser. No. 60/000,231 filed Jun. 15, 1995; U.S. Ser. No. 08/412,396 filed Mar. 28, 1995, abandoned, which is a continuation in part of U.S. Ser. No. 08/334,720 filed Nov. 4, 1994 now abandoned.

BACKGROUND OF THE INVENTION

The present invention relates to mixtures of herbicides that have a synergistic effect on weeds and which are safe to crop plants.

The control of undesired vegetation is extremely important in achieving high crop efficiency. This can be achieved by the selective control of the growth of weeds in such useful crops as rice, soybean, sugarbeet, corn, potato, wheat, barley, alfalfa, tomato, pineapple and plantation crops such as citrus and sugarcane among others. Unchecked weed growth in such useful crops can cause significant reduction in productivity and thereby result in increased costs to the consumers. The control of undesired vegetation in noncrop areas is also important. The need for finding products that achieve such results continues to be commercially important.

German published patent application DE-4236475-A1 discloses mixtures of anilofos with other herbicides, but does not disclose the mixtures of this invention.

SUMMARY OF THE INVENTION

This invention relates to mixtures of herbicides that produce synergistic results. The herbicidal mixtures comprise herbicidally effective amounts of the compound of Formula I in admixture with herbicidally effective amounts of one or more of the compounds of Formulae IIa through IIo and agriculturally suitable salts thereof, provided that when a herbicidally effective amount of the compound of Formula IId is present in the mixture, the mixture also comprises a herbicidally effective amount of one or more compounds of Formulae IIa to IIc and IIe to IIo. This invention also relates to herbicidal compositions comprising effective amounts of the aforesaid mixtures and at least one of the following: surfactant, solid or liquid diluent. This invention also relates to a method of controlling undesired vegetation comprising applying to the locus of the undesired vegetation herbicidally effective amounts of the aforesaid mixtures.

The mixtures of the invention comprising the Formula I and Formulae IIa–o compounds are described below:

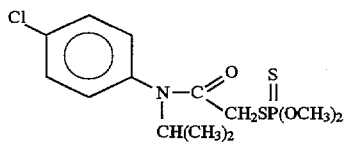

S-[2-[(4-chlorophenyl)(1-methylethyl)amino]-2-oxoethyl] O,O-dimethyl phosphorodithioate (anilofos, I);

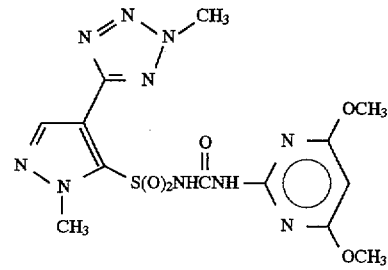

N-[[(4,6-dimethoxy-2-pyrimidinyl)amino]carbonyl]-1-methyl-4-(2-methyl-2H-tetrazol-5-yl)-1H-pyrazole-5-sulfonamide (azimsulfuron, IIa);

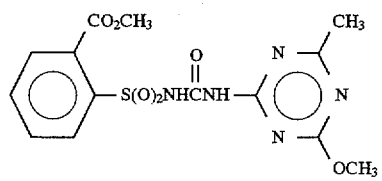

Methyl 2-[[[[(4-methoxy-6-methyl-1,3,5-triazin-2-yl) amino]carbonyl]amino]sulfonyl]benzoate (metsulfuron methyl, IIb);

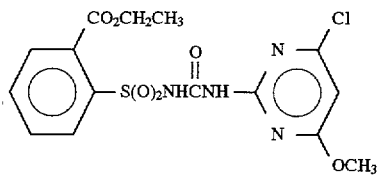

Ethyl 2-[[[[(4-chloro-6-methoxy-2-pyrimidinyl)amino] carbonyl]amino]sulfonyl]benzoate (chlorimuron ethyl, IIc);

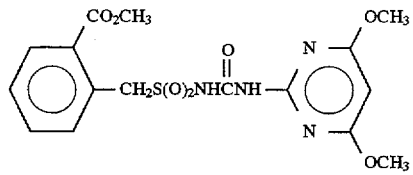

Methyl 2-[[[[[(4,6-dimethoxy-2-pyrimidinyl)amino] carbonyl]amino]sulfonyl]methyl]benzoate (bensulfuron methyl, IId);

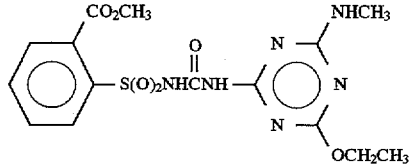

Methyl 2-[[[[[4-ethoxy-6-(methylamino)-1,3,5-triazin-2-yl]amino]carbonyl]amino]sulfonyl]benzoate (ethametsulfuron methyl, IIe);

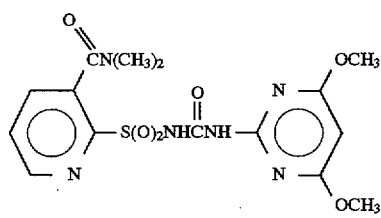

2-[[[[(4,6-dimethoxy-2-pyrimidinyl)amino]carbonyl]amino]sulfonyl]-N,N-dimethyl-3-pyridinecarboxamide (nicosulfuron, IIf);

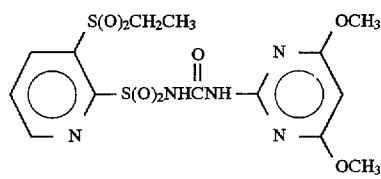

N-[[(4,6-dimethoxy-2-pyrimidinyl)amino]carbonyl]-3-(ethylsulfonyl)-2-pyridinesulfonamide (rimsulfuron, IIg);

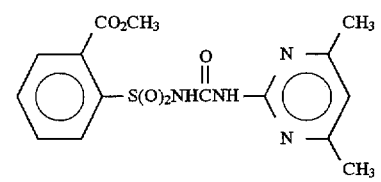

Methyl 2-[[[[(4,6-dimethyl-2-pyrimidinyl)amino]carbonyl]amino]sulfonyl]benzoate (sulfometuron methyl, IIh);

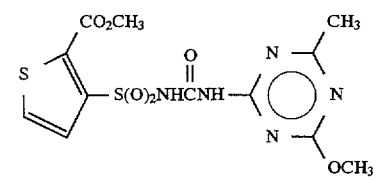

Methyl 3-[[[[(4-methoxy-6-methyl-1,3,5-triazin-2-yl)amino]carbonyl]amino]sulfonyl]-2-thiophenecarboxylate (thifensulfuron methyl, IIi);

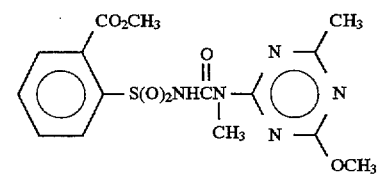

Methyl 2-[[[[(4-methoxy-6-methyl-1,3,5-triazin-2-yl)methylamino]carbonyl]amino]sulfonyl]benzoate (tribenuron methyl, IIj);

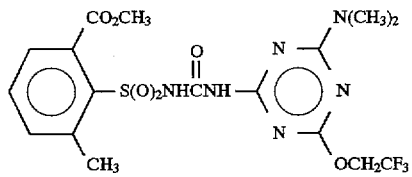

Methyl 2-[[[[[4-(dimethylamino)-6-(2,2,2-trifluoroethoxy)-1,3,5-triazin-2-yl]amino]carbonyl]amino]sulfonyl]-3-methylbenzoate (triflusulfuron methyl, IIk);

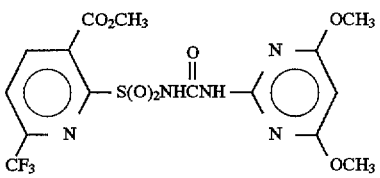

Methyl 2-[[[[(4,6-dimethoxy-2-pyrimidinyl)amino]carbonyl]amino]sulfonyl]-6-(trifluoromethyl)-3-pyridinecarboxylate (IIl);

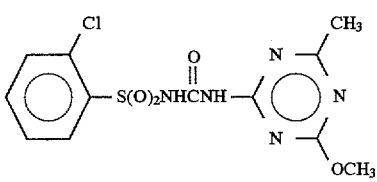

2-Chloro-N-[[4-methoxy-6-methyl-1,3,5-triazin-2-yl)amino]carbonyl]benzenesulfonamide (chlorsulfuron, IIm);

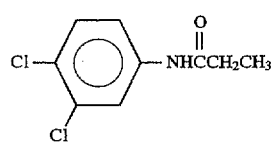

N-(3,4-dichlorophenyl)propanamide (propanil, IIn);

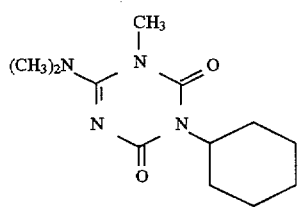

3-cyclohexyl-6-(dimethylamino)-1-methyl-1,3,5-triazine-2,4(1H,3H)-dione (hexazinone, IIo).

The mixtures of the invention preferred for enhanced herbicidal activity include:
a) the compound of Formula I and the compound of Formula IIa,
b) the compound of Formula I and compounds of Formulae IIa and IId,
c) the compound of Formula I and the compounds of Formulae IIb and IId,
d) the compound of Formula I and the compounds of Formulae IIb and IIc,
e) the compound of Formula I and the compound of Formula IIb,
f) the compound of Formula I and the compound of Formula IIe,
g) the compound of Formula I and the compound of Formula III,
h) the compound of Formula I and the compounds of Formulae IIb and III,
i) the compound of Formula I and the compound of Formula IIe,
j) the compound of Formula I and the compound of Formula IIf,
k) the compound of Formula I and the compound of Formula IIg, l) the compound of Formula I and compounds of Formulae IIg and IIi, m) the compound of Formula I and the compound of Formula IIh, n) the compound of Formula I and the compound of Formula IIi, o) the compound of Formula I and the compound of Formula IIj, p) the compound of Formula I and the compound of Formula IIk, q) the compound of Formula I and the compound of Formula IIm, r) the compound of Formula I and the compound of Formula IIn, and s) the compound of Formula I and the compound of Formula IIo.

The herbicidal compositions of the invention preferred for enhanced herbicidal activity include:

a) the compound of Formula I and the compound of Formula IIa, b) the compound of Formula I and compounds of Formulae IIa and IId, c) the compound of Formula I and the compounds of Formulae IIb and IId, d) the compound of Formula I and the compounds of Formulae IIb and IIc, e) the compound of Formula I and the compound of Formula IIb, f) the compound of Formula I and the compound of Formula IIc, g) the compound of Formula I and the compound of Formula III, h) the compound of Formula I and the compounds of Formulae IIb and III, i) the compound of Formula I and the compound of Formula IIe, j) the compound of Formula I and the compound of Formula IIf, k) the compound of Formula I and the compound of Formula IIg, l) the compound of Formula I and compounds of Formulae IIg and IIi, m) the compound of Formula I and the compound of Formula IIh, n) the compound of Formula I and the compound of Formula IIi, o) the compound of Formula I and the compound of Formula IIj, p) the compound of Formula I and the compound of Formula IIk, q) the compound of Formula I and the compound of Formula IIm, r) the compound of Formula I and the compound of Formula IIn, and s) the compound of Formula I and the compound of Formula IIo.

The mixtures of the invention most preferred for enhanced herbicidal activity include:

a) the compound of Formula I and the compound of Formula IIa, b) the compound of Formula I and compounds of Formulae IIa and IId, c) the compound of Formula I and the compounds of Formulae IIb and IId, d) the compound of Formula I and the compounds of Formulae IIb and IIc, e) the compound of Formula I and the compound of Formula IIb, and f) the compound of Formula I and the compound of Formula IIn.

The herbicidal compositions of the invention most preferred for enhanced herbicidal activity include:

a) the compound of Formula I and the compound of Formula IIa, b) the compound of Formula I and compounds of Formulae IIa and IId, c) the compound of Formula I and the compounds of Formulae IIb and IId, d) the compound of Formula I and the compounds of Formulae IIb and IIc, e) the compound of Formula I and the compound of Formula IIb, and f) the compound of Formula I and the compound of Formula IIn.

The preferred crops for application of the mixtures of the invention are rice, oilseed rape, barley, wheat, sugarbeet, corn, soybean, cotton, sugarcane, alfalfa, and pineapple. The mixtures are also useful for conifer release in forestry. The most preferred crops for application of mixtures of the invention are rice, oilseed rape, wheat, sugarbeet, corn, soybean and cotton.

DETAILS OF THE INVENTION

The Formula I compound can be prepared as described in U.S. Pat. No. 4,278,461. The synthesis involves the reaction of the chloroacetanilide of Formula 1 with the ammonium salt of Formula 2.

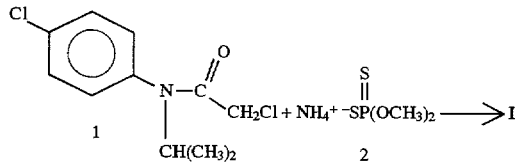

The Formula IIa compound can be prepared as described in U.S. Pat. No. 4,746,353. The synthesis involves the coupling of the pyrazole sulfonamide of Formula 3 with the heterocyclic carbamate of Formula 4.

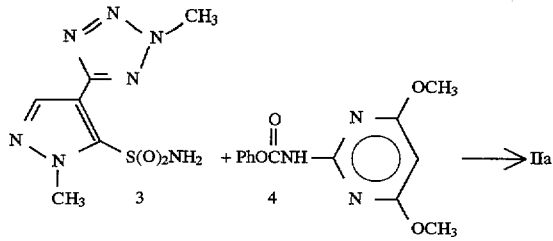

The Formula IIb compound can be prepared as described in U.S. Pat. No. 4,383,113. The synthesis involves the reaction of the sulfonyl isocyanate of Formula 5 with the heterocyclic amine of Formula 6.

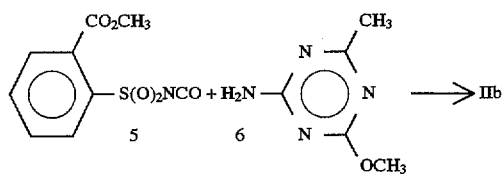

The Formula IIc compound can be prepared as described in U.S. Pat. No. 4,547,215. The synthesis involves the reaction of the sulfonyl isocyanate of Formula 7 with the heterocyclic amine of Formula 8.

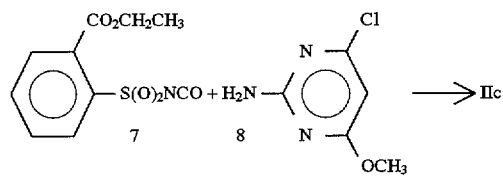

The Formula IId compound can be prepared as described in U.S. Pat. No. 4,420,325. The synthesis involves the reaction of the sulfonyl isocyanate of Formula 7 with the heterocyclic amine of Formula 8.

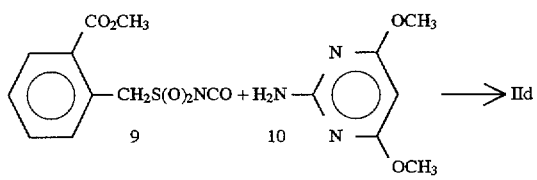

The Formula IIe compound can be prepared as described in U.S. Pat. No. 4,548,638. The synthesis involves the reaction of the sulfonyl isocyanate of Formula 5 with the heterocyclic amine of Formula 11.

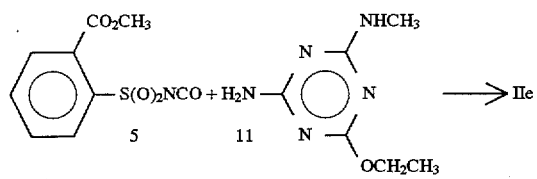

The Formula IIf compound can be prepared as described in U.S. Pat. No. 4,789,393. The synthesis involves the coupling of the pyridinesulfonamide of Formula 12 with the heterocyclic carbamate of Formula 4.

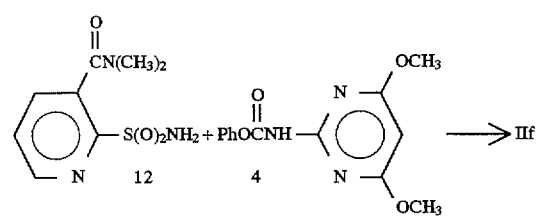

The Formula IIg compound can be prepared as described in U.S. Pat. No. 5,102,444 The synthesis involves the coupling of the pyridinesulfonamide of Formula 13 with the heterocyclic carbamate of Formula 4.

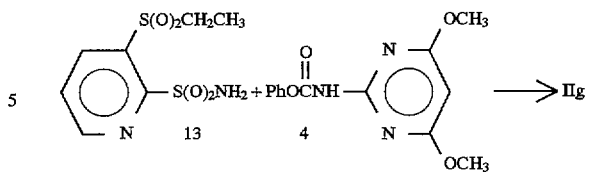

The Formula IIh compound can be prepared as described in U.S. Pat. No. 4,394,506. The synthesis involves reaction of the sulfonyl isocyanate of Formula 5 with the heterocyclic amine of Formula 14.

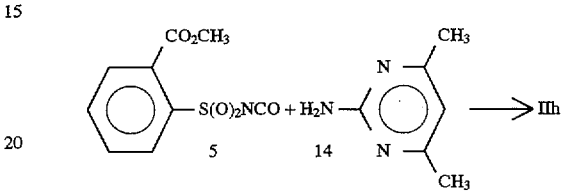

The Formula IIi compound can be prepared as described in U.S. Pat. No. 4,481,029. The synthesis involves reaction of the sulfonyl isocyanate of Formula 15 with the heterocyclic amine of Formula 6.

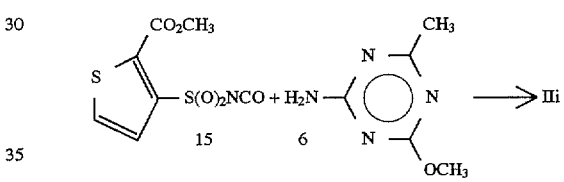

The Formula IIj compound can be prepared as described in U.S. Pat. No. 4,740,234. The synthesis involves reaction of the sulfonyl isocyanate of Formula 5 with the heterocyclic amine of Formula 16.

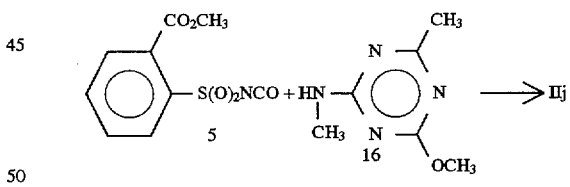

The Formula IIk compound can be prepared as described in U.S. Pat. No. 5,090,993. The synthesis involves the coupling of the N-silylsulfonamide of Formula 17 with the heterocyclic carbamate of Formula 18.

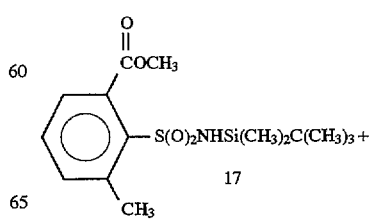

-continued

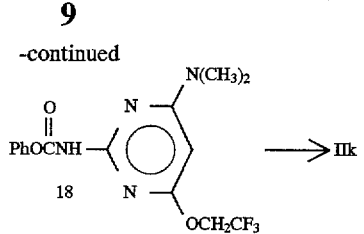

The Formula III compound can be prepared as described in WO92/15576. The synthesis involves the coupling of the pyridinesulfonamide of Formula 19 with the heterocyclic carbamate of Formula 4.

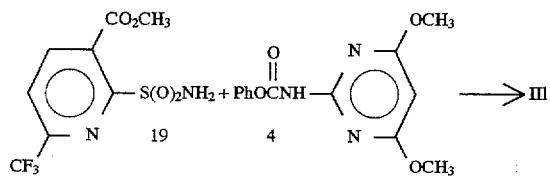

This reference also describes the preparation of the sodium salt of the Formula III compound by use of sodium methoxide.

The Formula IIm compound can be prepared as described in U.S. Pat. No. 4,127,405. The synthesis involves the reaction of the sulfonyl isocyanate of Formula 20 with the heterocyclic amine of Formula 6.

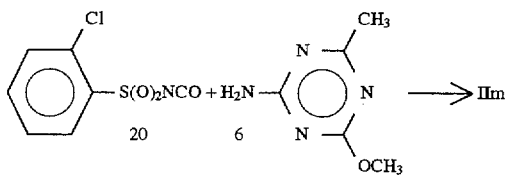

The Formula IIn compound can be prepared as described in U.S. Pat. No. 3,816,092. The synthesis involves reaction of 3,4-dichloroaniline with proprionyl chloride.

The Formula IIo compound can be prepared as described in U.S. Pat. No. 3,983,116. The synthesis involves reaction of the thioether of Formula 21 with dimethylamine.

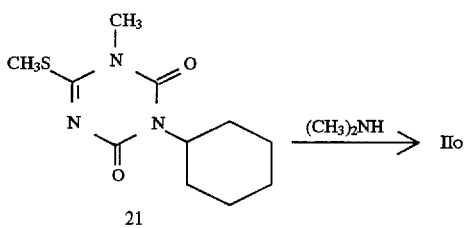

The mixtures of the present invention can include the sulfonylureas of Formulae IIa–m as one or more of their agriculturally suitable salts. These can be prepared in a number of ways known in the art. For example, metal salts can be made by contacting a sulfonylurea of Formulae IIa–m with a solution of an alkali or alkaline earth metal salt having a sufficiently basic anion (e.g., hydroxide, alkoxide, carbonate or hydride). Quaternary amine salts can be made by similar techniques.

Salts of the sulfonylureas of Formulae IIa–m can also be prepared by exchange of one cation for another. Cationic exchange can be effected by direct contact of an aqueous solution of a salt of a sulfonylurea of Formulae IIa–m (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a sulfonylurea of Formulae IIa–m (e.g., an alkali metal or quaternary amine salt) though a column packed with a cation-exchange resin containing the cation to be exchanged for that of the original salt and the desired product is eluted from the column. This method is particularly useful when the desired salt is water soluble (e.g., a potassium, sodium or calcium salt).

Formulation/Utility

The mixtures of the Formula I and Formula II compounds can be formulated in a number of ways:

(a) the Formula I and Formula II compounds can be formulated separately and applied separately or applied simultaneously in an appropriate weight ratio, e.g., as a tank mix; or (b) the Formula I and Formula II compounds can be formulated together in the proper weight ratio.

Mixtures of the Formula I and Formula II compounds will generally be used in formulation with an agriculturally suitable carrier comprising a liquid or solid diluent and/or a surfactant wherein the formulation is consistent with the physical properties of the active ingredients, mode of application and environmental factors such as soil type, moisture and temperature. Useful formulations include liquids such as solutions (including emulsifiable concentrates), suspensions, emulsions (including micro-emulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredients can be (micro) encapsulated and further formed into a suspension or solid formulation; alternatively the entire formulation of active ingredient can be encapsulated (or "overcoated"). Encapsulation can control or delay release of the active ingredients. Sprayable formulations can be extended in suitable media and used at spray volumes from about one to several hundred liters per hectare. High-strength compositions are primarily used as intermediates for further formulation.

The formulations will typically contain effective amounts of active ingredients, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J. as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillinite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Chemically stabilized aqueous sulfonylurea or agriculturally suitable sulfonylurea salt dispersions are taught in U.S. Pat. No. 4,936,900. Solution formulations of sulfonylureas with improved chemical stability are taught in U.S. Pat. No. 4,599,412. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp81–96; and Hance et al., *Weed Control Handbook*, 8th Ed., Blackwell Scientific Publications, Oxford, 1989.

In the following Examples, all percentages are by weight and all formulations are prepared in conventional ways. Formula numbers refer to the formulae identified on pages 2–5.

Example A

High Strength Concentrate

| | |
|---|---|
| Compound of Formula I | 92.9% |
| Compound of Formula IIa | 5.6% |
| silica aerogel | 0.5% |
| synthetic amorphous fine silica | 1.0%. |

Example B

Wettable Powder

| | |
|---|---|
| Compound of Formula I | 59.6% |
| Compound of Formula IIb | 1.2% |
| Compound of Formula IId | 4.2% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| Compound of Formula I | 9.2% |
| Compound of Formula IIb | 0.5% |
| Compound of Formula IIc | 0.3% |
| attapulgite granules (low volatile matter, 0.71/0.30 mm; U.S.S. No. 25–50 sieves) | 90.0%. |

Example D

Aqueous Suspension

| | |
|---|---|
| Compound of Formula I | 22.9% |
| Compound of Formula IIb | 2.1% |
| hydrated attapulgite | 3.0% |
| crude calcium ligninsulfonate | 10.0% |
| sodium dihydrogen phosphate | 0.5% |
| water | 61.5%. |

Example E

Extruded Pellet

| | |
|---|---|
| Compound of Formula I | 22.9% |
| Compound of Formula IIf | 2.1% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example F

High Strength Concentrate

| | |
|---|---|
| Compound of Formula I | 16.4% |
| Compound of Formula IIn | 82.1% |
| silica aerogel | 0.5% |
| synthetic amorphous fine silica | 1.0%. |

Example G

Granule

| | |
|---|---|
| Compound of Formula I | 9.2% |
| Compound of Formula III, sodium salt | 0.8% |
| attapulgite granules (low volatile matter, 0.71/0.30 mm; U.S.S. No. 25–50 sieves) | 90.0%. |

Example E

Extruded Pellet

| | |
|---|---|
| Compound of Formula I | 23.5% |
| Compound of Formula IIc | 1.5% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example G

Extruded Pellet

| | |
|---|---|
| Compound of Formula I | 21.2% |
| Compound of Formula IIe | 3.8% |

| | |
|---|---|
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example H

Extruded Pellet

| | |
|---|---|
| Compound of Formula I | 21.4% |
| Compound of Formula IIf | 3.6% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example I

Extruded Pellet

| | |
|---|---|
| Compound of Formula I | 22.5% |
| Compound of Formula IIg | 2.5% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example J

Extruded Pellet

| | |
|---|---|
| Compound of Formula I | 22.7% |
| Compound of Formula IIi | 2.3% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example K

Extruded Pellet

| | |
|---|---|
| Compound of Formula I | 22.7% |
| Compound of Formula IIj | 2.3% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example L

Extruded Pellet

| | |
|---|---|
| Compound of Formula I | 22.7% |
| Compound of Formula IIm | 2.3% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example M

Extruded Pellet

| | |
|---|---|
| Compound of Formula I | 22.7% |
| Compound of Formula IIk | 2.3% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example N

Extruded Pellet

| | |
|---|---|
| Compound of Formula I | 22.6% |
| Compound of Formula IIg | 1.6% |
| Compound of Formula IIi | 0.8% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example O

Extruded Pellet

| | |
|---|---|
| Compound of Formula I | 22.6% |
| Compound of Formula IIc | 1.2% |
| Compound of Formula IIf | 1.2% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example P

Extruded Pellet

| | |
|---|---|
| Compound of Formula I | 24.5% |
| Compound of Formula IIh | 0.5% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example Q

Extruded Pellet

| | |
|---|---|
| Compound of Formula I | 22.7% |
| Compound of Formula IIo | 2.3% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example R

Extruded Pellet

| | |
|---|---|
| Compound of Formula I | 24.4% |
| Compound of Formula IIb | 0.1% |
| Compound of Formula IId | 0.5% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example S

Extruded Pellet

| | |
|---|---|
| Compound of Formula I | 24.6% |
| Compound of Formula IIb | 0.2% |
| Compound of Formula IIc | 0.2% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example T

Extruded Pellet

| | |
|---|---|
| Compound of Formula I | 21.2% |
| Compound of Formula IIa | 0.7% |
| Compound of Formula IId | 3.1% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that mixtures of Formula I and Formula II mixtures are highly active herbicides, providing unexpected synergistic control of selected grass and broadleaf weeds. Many of the mixtures provide useful weed control when applied in sequential applications. Sequential applications of the mixtures may be particularly useful for controlling weeds that have germinated after the initial application or for improving control of larger weeds that may not be entirely controlled by a single application. In particular, sequential applications of the mixtures may be preferred in certain crop and non crop utilities. Specifically, sequential applications may be preferred in important agronomic crops which include but are not limited to sugar beet. Many of the mixtures also retain sufficient crop tolerance or even demonstrate safening on important agronomic crops, which include, but are not limited to, cotton, barley, wheat, corn (maize), alfalfa, potatoes, tomatoes, oilseed rape (including canola), sugar beets, soybeans, rice, pineapple, and sugarcane and other plantation crops. They are also useful for conifer release in forestry. The locus of application being a rice field, particularly a rice paddy, is a most preferred embodiment of this invention. Mixtures of this invention, including those with insufficient crop tolerance, have utility for enhanced broad-spectrum pre- and/or postemergence weed control in areas around fuel storage tanks, industrial storage areas, parking lots, drive-in theaters, billboards and highway and railroad structures. Alternatively, the subject mixtures are useful to modify plant growth.

The mixtures of Formula I with Formula IIa are particularly valued, because they retain acceptable levels of crop selectivity in certain major agronomic crops such as rice. The mixtures of Formula I with Formula IIb are particularly valued, because they retain acceptable levels of crop selectivity in certain major agronomic crops such as rice, barley and wheat. The mixtures of Formula I with Formula IIe are particularly valued, because they retain acceptable levels of crop selectivity in certain major agronomic crops such as oilseed rape (including 'Canola'), rice, barley and wheat. The mixtures of Formula I with Formulae IIi, IIj, III, and IIm are particularly valued, because they retain acceptable levels of crop selectivity in certain major agronomic crops such as barley and wheat. The mixtures of Formula I with Formula IIk are particularly valued, because they retain acceptable levels of crop selectivity in certain major agronomic crops such as sugar beet. The mixtures of Formula I with Formula IIf are particularly valued, because they retain acceptable levels of crop selectivity in certain major agronomic crops such as corn (maize), soybean and cotton containing at least one gene conferring resistance to inhibitors of acetolactate synthase. The mixtures of Formula I with Formula IIg alone or in combination with Formula IIi are particularly valued, because they retain acceptable levels of crop selectivity in certain major agronomic crops such as corn (maize) and cotton containing a least one gene conferring resistance to inhibitors of acetolactate synthase.

Lines, varieties and cultivars of corn (maize), soybean and cotton containing at least one gene conferring resistance to inhibitors of acetolactate synthase are commercially available (e.g., corn cult. 'P3180IR', soybean cult. 'W20') or can be produced by methods described in U.S. Pat. Nos. 4,761, 373, 5,013,659, 5,084,082, 5,084,086 and 5,159,135, and Sebastian et al., *Crop Sci.*, 1989, 29, 1403–1408.

In the context of this disclosure, a "line" is a group of plants of similar parentage that display little or no genetic variation between individuals for at least one trait. Such lines may be created by one or more generations of self-pollination and selection, or by vegetative propagation from a single parent, such as by tissue or cell culture techniques. A "variety" or "cultivar" refers to an agronomically superior line that has been extensively tested and is (or was) being used for commercial production.

The Formula I and Formula II mixtures of this invention can additionally be used in combination with other commercial herbicides, insecticides or fungicides. A mixture of one or more of the following herbicides with the Formula I and Formula II mixtures of this invention may be particularly useful for weed control. Examples of other herbicides as mixture partners are: acetochlor, acifluorfen and its sodium salt, acrolein (2-propenal), alachlor, ametryn, amidosulfuron, amitrole, ammonium sulfamate, asulam, atrazine, benazolin, benazolin-ethyl, benfluralin, benfuresate, bensulide, bentazone, bifenox, 2,6-bis[(4,6-dimethoxy-2-pyrimidinyl)oxy]benzoic acid, bromacil, bromoxynil, bromoxynil octanoate, butachlor, butralin, butylate, carbetamide, chlomethoxyfen, chloramben, chlorbromuron, chloridazon, chlornitrofen, 2-[4-chloro-5-(cyclopentyloxy)-2-fluorophenyl]-4,5,6,7-tetrahydro-1H-indene-1,3(2H)-dione (KPP-314), 3-[4-chloro-2-fluoro-5-(cyclopentyloxy)phenyl]-5-(1-methylethylidene)-2,4-oxazolidinedione, 3-[4-chloro-2-fluoro-5-(1-methyl-2-propynyloxy)phenyl]-5-(1-methylethylidene]-2,4-oxaxolidinedione, 2-[[2-(3-chlorophenyl)-2-oxiranyl]methyl]-2-ethyl-1H-indene-1,3(2H)-dione (MK-243), chlorotoluron, chlorpropham, chlorthal-dimethyl, clopyralid, cinmethylin, cinosulfuron, clethodim, clomazone, clopyralid, clopyralid-olamine, cyanazine, cycloate, N-[[[2-(cyclopropylcarbonyl)phenyl]amino]sulfonyl]-N'-(4,6-dimethoxy-2-pyrimidinyl)urea, cyclosulfamuron, cycloxydim, 2,4-D and its butotyl, butyl, isoctyl and isopropyl esters and its dimethylammonium, diolamine and trolamine salts, cyhalofop-butyl, daimuron, dalapon, dalapon-sodium, dazomet, 2,4-DB and its dimethylammonium, potassium and sodium salts, desmedipham, desmetryn, dicamba and its dimethylammonium, potassium and sodium salts, dichlobenil, 3-[1-(3,5-dichlorophenyl)-1-methylethyl]-2,3-dihydro-6-methyl-5-phenyl-4H-1,3-oxazin-4-one, 3-[2,4-dichloro-5-(2-propynyloxy)phenyl]-5-(1,1-dimethylethyl)-1,3,4-oxadiazol-2(3H)-one, dichlorprop, diclofop-methyl, N,N-diethyl-3-[(2,4,6-trimethylphenyl)sulfonyl]-1H-1,2,4-triazole-1-carboxamide (CH 900), difenzoquat metilsulfate, diflufenican, dimefuron, 6-[[6,7-dihydro-6,6-dimethyl-3H,5H-pyrrolo[2,1-c][1,2,4]thiadiazol-3-ylidine]amino]-7-fluoro-4-(2-propynyl)-2H-1,4-benzoxazin-3(4H)-one, dimepiperate, dimethylarsinic acid and its sodium salt, dinitramine, diphenamid, diquat dibromide, dithiopyr, diuron, DNOC, endothal, EPTC, esprocarb, ethalfluralin, ethofumesate, ethyl[2-chloro-5-[4-chloro-5-(difluoromethoxy)-1-methyl-1H-pyrazol-3-yl]-4-fluorophenoxy]acetate, ethyl α,2-dichloro-5-[4-(difluoromethyl)-4,5-dihydro-3-methyl-5-oxo-1H-1,2,4-triazol-1-yl]-4-fluorobenzenepropanoate, etobenzanid, fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumicloracpentyl, flumioxazin, fluometuron, fluoroglycofen-ethyl, flupoxam, fluridone, flurochloridone, fluroxypyr, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, metazachlore, methabenzthiazuron, methyl[[2-chloro-4-fluoro-5-[(tetrahydro-3-oxo-1H,3H-[1,3,4]thiadiazolo[3,4-α]pyridazin-1-ylidene)amino]phenyl]thio]acetate (KIH 9201), methylarsonic acid and its calcium, monoammonium, monosodium and disodium salts, methyl[[[1-[5-[2-chloro-4-(trifluoromethyl)phenoxy]-2-nitrophenyl]-2-methoxyethylidene]amino]oxy]acetate (AKH-7088), methyl 3-chloro-5-[[[[4,6-dimethoxy-2-pyrimidinyl)amino]carbonyl]amino]sulfonyl]-1-methyl-1H-pyrazole-4-carboxylate, methyl 2-[(4,6-dimethoxy-2-pyrimidinyl)oxy]-6-[1-(methoxyimino)ethyl]benzoate (KIH 6127), methyl 5-[[[[(4,6-dimethyl-2-pyrimidinyl)amino]carbonyl]amino]

sulfonyl]-1-(2-pyridinyl)-1H-pyrazole-4-carboxylate (NC-330), N-(4-fluoro-phenyl)-N-(1-methylethyl)-2-[[5-(trifluoromethyl)-1,3,4-thiadiazol-2-yl]oxy]acetamide, metobenzuron, metolachlor, metoxuron, metribuzin, metsulfuron-methyl, molinate, monolinuron, napropamide, naptalam, neburon, norflurazon, oryzalin, oxadiazon, oxyfluorfen, paraquat dichloride, pebulate, pendimethalin, perfluidone, phenmedipham, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyributicarb, pyridate, quinclorac, quinmerac, quizalofop-ethyl, quizalofop-P-ethyl, quizalofop-P-tefuryl, sethoxydim, siduron, simazine, sulfentrazone, TCA, TCA-sodium, tebutame, tebuthiuron, terbacil, terbuthylazine, terbutryn, thenylchlor, thiobencarb, tralkoxydim, tri-allate, triasulfuron, triclopyr, triclopyr-butotyl, triclopyr-triethylammonium, tridiphane, trifluralin, and vernolate.

For mixtures of the compound of Formula I with the compounds of Formula IIa or Formula IIn, the following herbicide mixture partners are particularly useful: bensulfuron methyl, butachlor, 3-[1-(3,5-dichlorophenyl)-1-methylethyl]-2,3-dihydro-6-methyl-5-phenyl-4H-1,3-oxazin-4-one, methyl 2-[(4,6-dimethoxy-2-pyrimidinyl)oxy]-6-[1-(methoxyimino)ethyl]benzoate (KIH 6127), molinate, 2-[[2-(3-chlorophenyl)-2-oxiranyl]methyl]-2-ethyl-1H-indene-1,3(2H)-dione (MK-243), cinosulfuron, N,N-diethyl-3-[(2,4,6-trimethylphenyl)sulfonyl]-1H-1,2,4-triazole-1-carboxamide (CH 900), etobenzanid, mefenacet, pretilachlor, pyrazosulfuron methyl, pyributicarb and thiobencarb.

For mixtures of the compound of Formula I with the compound of Formula IIe, the following herbicide mixture partners are particularly useful: barban, benazolin, carbetamid, clopyralid, cyanazine, cycloxydim, dimefuron, fluazifop, haloxyfop, isoxaben, metazachlore, napropamide, propaquizafop, propyzamide, pyridate, quizalofop, sethoxydim, TCA, tebutame, and trifluralin.

For mixtures of the compound of Formula I with the compounds of Formula IIb, Formula IIi, Formula IIj, Formula III or Formula IIm, besides combinations of the compounds of Formulae IIb, IIi, IIj, III and IIm themselves, the following herbicide mixture partners are particularly useful: amidosulfuron, 3-chloro-5-[[[(4,6-dimethoxy-2-pyrimidinyl)amino]carbonyl]amino]sulfonyl]-1-methyl-1H-pyrazole-4-carboxylate, cinosulfuron, N-[[[2-(cyclopropylcarbonyl)phenyl]amino]sulfonyl]-N'-(4,6-dimethoxy-2-pyrimidinyl)urea, imazamethabenz, mefluidide, prosulfuron and triasulfuron, and herbicides with a similar spectrum of control but a different mode of action such as, but not limited to: barban, bentazon, bifenox, bromoxynil, bromoxynil heptanoate, bromoxynil octanoate, chloridazon, 2-[4-chloro-5-(cyclopentyloxy)-2-fluorophenyl]-4,5,6,7-tetrahydro-1H-indene-1,3(2H)-dione, 3-[4-chloro-2-fluoro-5-(1-methyl-2-propynyloxy)phenyl]-5-(1-methylethylidene)-2,4-oxazolidinedione, chlortoluron, clodinafop, clopyralid, cyanazine, cyhalofop-butyl, dicamba, diclofop, dichlorprop, diclofop, difenzoquat, diflufenican, 6-[[6,7-dihydro-6,6-dimethyl-3H,5H-pyrrolo[2,1-c]-[1,2,4]thiadiazol-3-ylidine]amino]-7-fluoro-4-(2-propynyl)-2H-1,4-benzoxazin-3(4H)-one, ethyl[2-chloro-5-[4-chloro-5-(difluoromethoxy)-1-methyl-1H-pyrazol-3-yl]-4-fluorophenoxy]acetate, ethyl α,2-dichloro-5-[4-(difluoromethyl)-4,5-dihydro-3-methyl-5-oxo-1H-1,2,4-triazol-1-yl]-4-fluorobenzenepropanoate, fenoxaprop, flamprop, N-(4-fluorophenyl)-N-(1-methylethyl)-2-[[5-(trifluoromethyl)-1,3,4-thiadiazol-2-yl]oxy]acetamide, fluoxypyr, flupoxam, fluridone, flurtamone, glufosinate, glyphosate, ioxynil, isoproturon, isoxaben, MCPA, MCPA-thioethyl, MCPB, mecoprop, mecoprop-P, methabenzthiazuron, methyl metribuzin, pendimethalin, tri-allate, tralkoxydim, trifluralin, (2,4-dichlorophenoxy)acetic acid, and 4-(2,4-dichlorophenoxy)butanoic acid.

For mixtures of the compound of Formula I with the compound of Formula IIi, the following herbicide mixture partners are also particularly useful: chlorimuron ethyl, cloransulam methyl, 2-[4,5-dihydro-4-methyl-4-(1-methylethyl)-5-oxo-1H-imidazol-2-yl]-5-(methoxymethyl)-3-pyridinecarboxylic acid, flumetsulam, halosulfuron, imazaquin, imazethapyr, nicosulfuron, 3-oxetanyl 2-[[[[(4,6-dimethyl-2-pyrimidinyl)amino]sulfonyl]benzoate, prosulfuron, pyrithiobac sodium and rimsulfuron, and herbicides with a similar spectrum of control but a different mode of action such as, but not limited to: acetochlor, acifluorfen, alachlor, atrazine, benazolin, bentazon, butylate, methyl[[2-chloro-4-fluoro-5-[(5,6,7,8-tetrahydro-3-oxo-1H,3H-[1,3,4]thiadiazolo[3,4-a]pyridazin-1-ylidene)amino]phenyl]thio]acetate, clethodim, clomazone, clopyralid, cyanazine, 2,4-D, 2,4-DB, dicamba, α,2-dichloro-5-[4-(difluoromethyl)-4,5-dihydro-3-methyl-5-oxo-1H-1,2,4-triazol-1-yl]-4-fluorobenzenepropanoate, dimethenamid, disodium metharsonate, diuron, EPTC, ethalfluralin, fenoxaprop, fluazifop, fluazifop-P, fluminclorac pentyl ester, flumioxazin, fluometuron, fomesafen, glufosinate, glyphosate, haloxyfop, isoxaflutole, lactofen, linuron, MCPA, metolachlor, metribuzin, mefluidide, monosodium metharsonate, norfluazon, paraquat, pendimethalin, pyridate, quizalofop-ethyl, quizalofop-P-ethyl, sethoxydim, simazine, sulcotrione, thiafluamide, tridiphane, trifluralin and vernolate.

For mixtures of the compound of Formula I with the compounds of Formula IIc, Formula IIf and Formula IIg, besides combinations of the compounds of Formulae IIc, IIf and IIg themselves, the following herbicide mixture partners are particularly useful: cloransulam methyl, 2-[4,5-dihydro-4-methyl-4-(1-methylethyl)-5-oxo-1H-imidazol-2-yl]-5-(methoxymethyl)-3-pyridinecarboxylic acid, flumetsulam, halosulfuron, imazaquin, imazethapyr, 3-oxetanyl 2-[[[[(4,6-dimethyl-2-pyrimidinyl)amino]carbonyl]amino]sulfonyl]benzoate, primisulfuron, prosulfuron, pyrithiobac sodium and thifensulfuron methyl, and herbicides with a similar spectrum of control but a different mode of action such as, but not limited to: acetochlor, acifluoren, alachlor, atrazine, benazolin, bentazon, butylate, methyl[[2-chloro-4-fluoro-5-[(5,6,7,8-tetrahydro-3-oxo-1H,3H-[1,3,4]thiadiazolo[3,4-a]pyridazin-1-ylidene)amino]phenyl]thio]acetate, clethodim, clomazone, clopyralid, cyanazine, 2,4-D, 2,4-DB, dicamba, α,2-dichloro-5-[4-(difluoromethyl)-4,5-dihydro-3-methyl-5-oxo-1H-1,2,4-triazol-1-yl]-4-fluorobenzenepropanoate, dimethenamid, disodium metharsonate, diuron, EPTC, ethalfluralin, fenoxaprop, fluazifop, fluazifop-P, fluminclorac pentyl ester, flumioxazin, fluometuron, fomesafen, glufosinate, glyphosate, haloxyfop, isoxaflutole, lactofen, linuron, MCPA, metolachlor, metribuzin, mefluidide, monosodium metharsonate, norfluazon, paraquat, pendimethalin, pyridate, quizalofop-ethyl, quizalofop-P-ethyl, sethoxydim, simazine, sulcotrione, thiafluamide, tridiphane, trifluralin and vernolate.

For mixtures of the compound of Formula I with the compound of Formula IIh, the following herbicide mixture partners are also particularly useful: ammonium fosamine, chlorsulfuron, diuron, glufosinate, glyphosate, metsulfuron methyl, norfluazon, oryzalin, oxyfluorfen, paraquat, terbacil and simazine.

For mixtures of the compound of Formula I with the compound of Formula IIk, the following herbicide mixture partners are also particularly useful: alloxydim-sodium, barban, chloridazon, chlorpropham, cycloate, cycloxidim, dalapon, desmedipham, diallate, diclofop, diethatyl ethyl, diquat, endothall, EPTC, ethofumesate, fenuron, fluazifop, glufosinate, glyphosate, lenacil, metamitron, paraquat, pebulate, phenmedipham, propham, quinmerac, quizalofop, sethoxydim, TCA, triallate and trifluralin.

For mixtures of the compound of Formula I with the compound of Formula IIo, the following herbicide mixture partners are also particularly useful: ametryn, asulam, atrazine, bromacil, diuron, metribuzin, norfluazon, pendimethalin, terbacil and trifluralin.

Mixtures of the compound of Formula I with mixtures of the compounds of Formulae IIa and IId are particularly useful, especially when the weight ratio of the compound of Formula IIa to the compound of Formula IId is about 1:4 to 1:5. Mixtures of the compound of Formula I with mixtures of the compounds of Formulae IIb and IIc are particularly useful, especially when the weight ratio of the compound of Formula IIb to the compound of Formula IIc is about 1:1. Mixtures of the compound of Formula I with mixtures of the compounds of Formulae IIb and IId are particularly useful, especially when the weight ratio of the compound of Formula IIb to the compound of Formula IId is about 1:5. Mixtures of the compound of Formula I with mixtures of the compounds of Formulae IIg and IIi are particularly useful, especially when the weight ratio of the compound of Formula IIg to the compound of Formula IIi is about 2:1. Mixtures of the compound of Formula I with mixtures of the compounds of Formulae IIc and IIf are also particularly useful.

In certain instances, combinations with other herbicides having a similar spectrum of control but a different mode of action will be particularly advantageous for resistance management.

Generally, the herbicidally effective amounts of the compounds of Formula I and Formula II in the mixtures will vary depending on the specific compounds selected, environmental conditions, formulation, method of application, amount and type of vegetation present, etc. The herbicidally effective amounts of Formula I relative to Formula IIa–m compounds are generally in a ratio of 4000:1 to 1:10, the ratio of the Formula I to Formula IIn compound is generally 5:1 to 1:500, and the ratio of the Formula I to Formula IIo compound is generally 100:1 to 1:10. Preferably, the herbicidally effective amounts of Formula I relative to Formula IIa–m compounds are generally in a ratio of 600:1 to 10:7. More specifically, the herbicidally effective amounts of Formula I relative to Formula IIa are preferably in a ratio of 75:1 to 1:2, with the most preferred ratios being 19:1 to 3:1. Preferably, the herbicidally effective amounts of Formula I relative to Formula IIb are in a ratio of 250:1 to 1:1, with the most preferred ratios being 75:1 to 25:1. Preferably, the herbicidally effective amounts of Formula I relative to Formula IIc are in a ratio of 250:1 to 1:1, with the most preferred ratios being 60:1 to 4:1. Preferably, the herbicidally effective amounts of Formula I relative to Formula IIe are in a ratio of 250:1 to 1:1, with the most preferred ratios being 20:1 to 2:1. Preferably, the herbicidally effective amounts of Formula I relative to Formula IIf are in a ratio of 75:1 to 1:2, with the most preferred ratios being 25:1 to 2:1. Preferably, the herbicidally effective amounts of Formula I relative to Formula IIg are in a ratio of 100:1 to 1:1, with the most preferred ratios being 25:1 to 4:1. Preferably, the herbicidally effective amounts of Formula I relative to Formula IIh are in a ratio of 250:1 to 2:1, with the most preferred ratios being 150:1 to 15:1. Preferably, the herbicidally effective amounts of Formula I relative to Formula IIi are in a ratio of 250:1 to 1:1, with the most preferred ratios being 30:1 to 4:1. Preferably, the herbicidally effective amounts of Formula I relative to Formula IIj are in a ratio of 250:1 to 1:1, with the most preferred ratios being 30:1 to 4:1. Preferably, the herbicidally effective amounts of Formula I relative to Formula IIk are in a ratio of 250:1 to 1:2, with the most preferred ratios being 30:1 to 4:1. Preferably, the herbicidally effective amounts of Formula I relative to Formula IIl are in a ratio of 250:1 to 1:1, with the most preferred ratios being 50:1 to 10:1. Preferably, the herbicidally effective amounts of Formula I relative to Formula IIm are in a ratio of 250:1 to 1:1, with the most preferred ratios being 30:1 to 4:1. Preferably, the herbicidally effective amounts of Formula I relative to Formula IIn are in a ratio of 2:1 to 1:200, with the most preferred ratios being 1:1 to 1:50. Preferably, the herbicidally effective amounts of Formula I relative to Formula IIo are in a ratio of 50:1 to 1:1, with the most preferred ratios being 30:1 to 2:1.

Generally a herbicidally effective amount of the Formula I compound is applied at a rate from 5 to 2000 g ai/ha, and, in general, the herbicidally effective amount of each Formula IIa–m compound present in the mixture is applied at a rate from 0.25 to 200 g ai/ha, and the Formula IIn compound, if present, is applied at a rate of 150 to 5000 g/ha, and the Formula IIo compound, if present, is applied at a rate of 10 to 2000 g ai/ha. Preferably, the Formula I compound is applied at a rate from 40 to 600 g ai/ha, and, in general, and each Formula IIa–m compound present is applied at a rate from 1 to 35 g ai/ha. Preferably, the Formula IIa compound is applied at a rate from 0.5 to 50 g ai/ha, and most preferably at rate from 6 to 32 g ai/ha. Preferably, the Formula IIb compound is applied at a rate from 0.5 to 100 g ai/ha, and most preferably at rate from 1 to 20 g ai/ha. Preferably, the Formula IIc compound is applied at a rate from 1 to 35 g ai/ha, and most preferably at rate from 2 to 20 g ai/ha. Preferably, the Formula IIe compound is applied at a rate from 0.5 to 100 g ai/ha, and most preferably at rate from 5 to 30 g ai/ha. Preferably, the Formula IIf compound is applied at a rate from 1 to 200 g ai/ha, and most preferably at rate from 4 to 100 g ai/ha. Preferably, the Formula IIg compound is applied at a rate from 0.5 to 100 g ai/ha, and most preferably at rate from 2 to 50 g ai/ha. Preferably, the Formula IIh compound is applied at a rate from 0.25 to 70 g ai/ha, and most preferably at rate from 0.5 to 20 g ai/ha. Preferably, the Formula IIi compound is applied at a rate from 0.5 to 100 g ai/ha, and most preferably at rate from 2 to 50 g ai/ha. Preferably, the Formula IIj compound is applied at a rate from 0.5 to 100 g ai/ha, and most preferably at rate from 5 to 30 g ai/ha. Preferably, the Formula IIk compound is applied at a rate from 0.5 to 100 g ai/ha, and most preferably at rate from 5 to 30 g ai/ha. Preferably, the Formula IIl compound is applied at a rate from 0.5 to 100 g ai/ha, and most preferably at rate from 1 to 40 g ai/ha. Preferably, the Formula IIm compound is applied at a rate from 0.5 to 100 g ai/ha, and most preferably at rate from 5 to 30 g ai/ha. Preferably, the Formula IIn compound is applied at a rate from 200 to 4000 g ai/ha, and most preferably at a rate from 200 to 3000 g ai/ha. Preferably, the Formula IIo compound is applied at a rate from 15 to 1000 g ai/ha, and most preferably at rate from 20 to 200 g ai/ha. For best synergistic control of *Cyperus difformis* and *Cyperus iria* by mixtures of Formula I and Formula IIa, the Formula I compound is applied at application rates less than 50 g ai/ha and the Formula IIa compound is applied at application rates less than 2 g ai/ha. For best synergistic control of *Cyperus iria* by mixtures of Formula I and Formula IIc, the Formula I compound is applied at applications rates greater than 25 g ai/ha and the Formula IIc compound is applied at application rates less than 2 g ai/ha. For best synergistic control of *Heteranthera limosa* by mixtures of Formula I, Formula IIb and Formula IIc, the Formula I compound is applied at application rates greater than 50 g ai/ha. For best synergistic control of *Heteranthera limosa* by mixtures of Formula I, Formula IIb and Formula IId, the Formula I compound is applied at application rates greater than 25 g ai/ha, the Formula IIb compound is applied at application rates greater than 0.1 g ai/ha and the Formula IId compound is applied at application rates greater than 0.5 g ai/ha. For best synergistic control of *Sinapsis arvensis* by mixtures of Formula I and Formula IIh, the mixtures are applied preemergence. For best synergistic control of *Echinochloa crus-galli* by mixtures of Formula I and Formula IIh, the mixtures are applied preemergence and the Formula I compound is applied at application rates greater than 32 g ai/ha and less than 250 g ai/ha. For best synergistic control of *Echinochloa crus-galli* by mixtures of Formula I and Formula IIn, the Formula I compound is applied at application rates greater than 50 g ai/ha. One skilled in the art can readily determine herbicidally effective application rates and ratios of the herbicide of Formula I to the herbicides of Formula II as well as timing necessary for the desired level of weed control and crop safety.

The Formula I phosphorodithioate (Compound 1) was tested in combination with the Formula IIa sulfonylurea (Compound 2), the Formula IIb sulfonylurea (Compound 3), the sodium salt of the Formula III sulfonylurea (Compound 4), the Formula III sulfonylurea (Compound 5), the Formula IIj sulfonylurea (Compound 6) the Formula IIm sulfonylurea (Compound 7), the Formula IIe sulfonylurea (Compound 8), the Formula IIf sulfonylurea (Compound 9), the Formula IIg sulfonylurea (Compound 10), the Formula IIc sulfonylurea (Compound 11), the Formula IIk sulfonylurea (Compound 12), the Formula IIn propanamide (Compound 13), the Formula IIh sulfonylurea (Compound 14), the Formula IIo triazinedione (Compound 15), and the Formula IId sulfonylurea (Compound 16). The compounds of Formula I and Formula II are listed below by number referred to in the following test data:

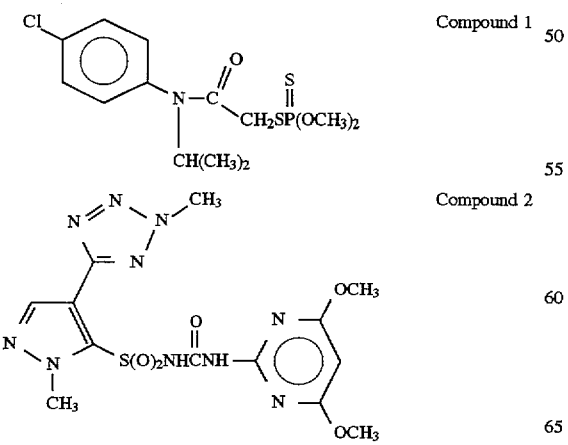

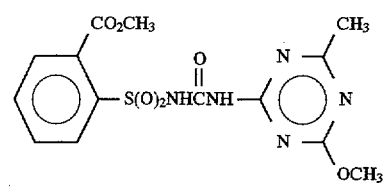

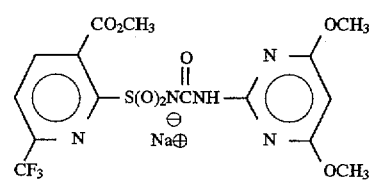

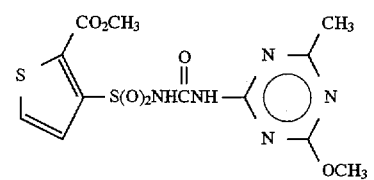

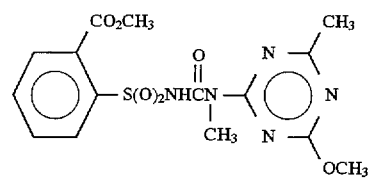

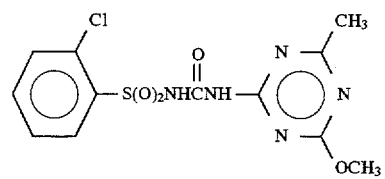

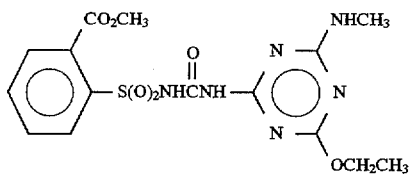

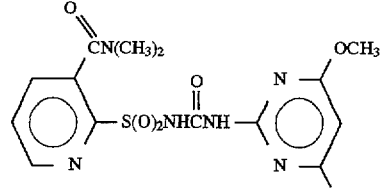

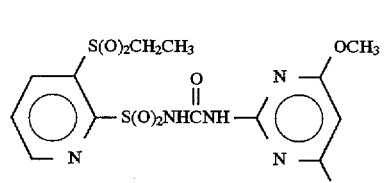

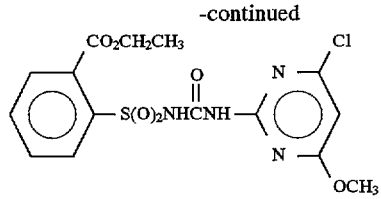

Compound 11

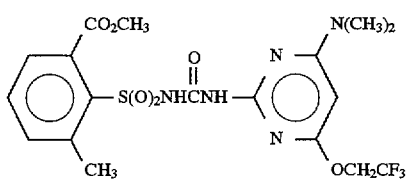

Compound 12

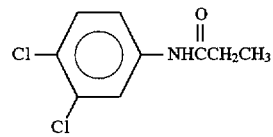

Compound 13

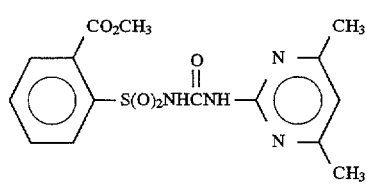

Compound 14

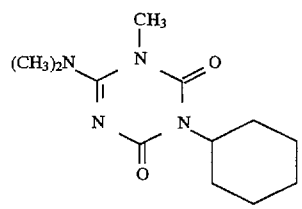

Compound 15

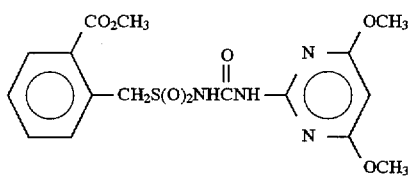

Compound 16

The following test protocol was used for the test in Table A. Compound numbers are as described above. The data demonstrate the efficacy of the Formula I and Formula IIa mixtures of this invention against a specific weed. The weed control afforded by the mixtures of this invention are not limited, however, to this species.

Test A Protocol

Plastic pots were partially filled with silt loam soil. The soil was then flooded with water, and 1.5–2.0-leaf transplants of rice (*Oryza sativa*) tropical japonica cult. 'Cypress' were planted in the soil. Seeds of barnyardgrass (*Echinochloa crus-galli*) were planted in saturated soil, and the plants grown to the 2-leaf stage for testing. At treatment time, the water level for all plantings was raised to 3 cm above the soil surface. Chemical treatments were formulated in a non-phytotoxic solvent mixture containing a surfactant and applied directly to the paddy water. These treatments were replicated twice. Treated plants and controls were maintained in a greenhouse for 24 days, after which time all species were compared to controls and visually evaluated. Plant response ratings, summarized in Table A are reported on a 0 to 100 scale where 0 is no effect and 100 is complete control.

For Test A, the mean response of each treatment was determined. Colby's equation was used to calculate the expected additive herbicidal effect of the mixtures of Compound 1 and Compound 2. Colby's equation (Colby, S. R. "Calculating Synergistic and Antagonistic Responses of Herbicide Combinations," Weeds, 15(1), pp 20–22 (1967)) calculates the expected additive effect of herbicidal mixtures, and for two active ingredients is of the form:

$$P_{a+b} = P_a + P_b - (P_a P_b / 100)$$

wherein $P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

Results of Test A are shown in Table A, which lists the mean response of a specific weed to Compound 1 and Compound 2 applied alone as single active ingredients, applied as a mixture of Compound 1 and Compound 2, and the expected additive effect of the herbicidal mixture of Compound 1 and Compound 2 (from Colby's equation). Weeds other than those specifically listed are also controlled by mixtures of Compound 1 and Compound 2. Different ratios of Compound 1 to Compound 2, and different formulation types, also provide useful weed control from the combination of the two herbicides.

TABLE A*

| | | Effect of Compound 1 and Compound 2 as Active Ingredients Alone and in Mixture | | | |
|---|---|---|---|---|---|
| Compound 1 | Compound 2 | Rice (3.5 L.S.) | | Barnyardgrass (2 L.S.) | |
| | | Mean | Expected† | Mean | Expected |
| Alone | | | | | |
| 25 | 0 | 0 | — | 23 | — |
| 50 | 0 | 0 | — | 38 | — |
| 150 | 0 | 0 | — | 68 | — |
| 0 | 2 | 0 | — | 5 | — |
| 0 | 4 | 0 | — | 10 | — |
| 0 | 8 | 0 | — | 43 | — |
| 0 | 16 | 5 | — | 83 | — |
| Mixtures | | | | | |
| 25 | 2 | 0 | 0 | 0 | 27 |
| 50 | 2 | 0 | 0 | 38 | 41 |
| 150 | 2 | 0 | 0 | 80 | 70 |
| 25 | 4 | 0 | 0 | 5 | 31 |
| 50 | 4 | 0 | 0 | 25 | 34 |
| 150 | 4 | 0 | 0 | 73 | 72 |
| 25 | 8 | 15 | 0 | 95 | 56 |
| 50 | 8 | 20 | 0 | 77 | 65 |
| 150 | 8 | 30 | 0 | 99 | 82 |
| 25 | 16 | 33 | 5 | 95 | 87 |
| 50 | 16 | 38 | 5 | 98 | 90 |
| 150 | 16 | 38 | 5 | 99 | 95 |

*Application rates are expressed in g ai/ha for both Compound 1 and Compound 2. Data are reported as percent control.
†Colby, S. R. "Calculating Synergistic and Antagonistic Responses of Herbicide Combinations," Weeds, 15(1), pp 20–22 (1967).

The following protocol was used for the test in Table B. Compound numbers are as described on page 28. The data demonstrate the efficacy of the Formula I and Formula IIb mixtures, mad Formula I and Formula III mixtures of this invention against specific weeds. The weed control afforded by the mixtures of this invention are not limited, however, to these species.

Test B Protocol

*Triticum aestivum* cult. 'Recital' (TRZAS-R) (winter wheat), *Triticum aestivum* cult. 'Era' (TRZAS-E) (spring wheat), *Aegilops cylindrica* (AEGCY), *Bromus tectorum* (BROTE), *Lolium multiflorum* (LOLMU), *Avena fatua* (AVEFA), *Setaria viridis* (SETVI), *Kochia scoparia* (KCHSC), *Apera spica-venti* (APESV), *Phalaris minor* (PHAMI), *Alopecurus myosuroides* (ALOMY), and *Poa annua* (POAAN) were grown in a greenhouse to approximately the two-leaf stage in 17-cm diameter round fiber pots filled with a mixture of 60% sandy loam soil and 40% Metro-Mix 350™ growing medium. Compound 1 was formulated as a single active ingredient in 30% emulsifiable concentrate. Compound 3 was formulated as a single active ingredient in 60% strength dry flowable granules. Compound 4 was formulated as a single active ingredient in 50% strength dry flowable granules. Treatments were applied to the test species by diluting the compounds in a non-phytotoxic solvent, and spraying the treatments onto the plants. Compound 1 was applied at 62, 125, 250, and 500 g ai/ha. Compound 3 was applied at 4 g ai/ha. Compound 4 was applied at 8 g ai/ha. Mixtures of Compound 1 at 62 g ai/ha and Compound 3 at 4 g ai/ha, Compound 1 at 125 g ai/ha and Compound 3 at 4 g ai/ha, Compound 1 at 250 g ai/ha and Compound 3 at 4 g ai/ha, Compound 1 at 500 g ai/ha and Compound 3 at 4 g ai/ha, Compound 1 at 62 g ai/ha and Compound 4 at 8 g ai/ha, Compound 1 at 125 g ai/ha and Compound 4 at 8 g ai/ha, Compound 1 at 250 g ai/ha and Compound 3 at 4 g ai/ha, and Compound 1 at 500 g ai/ha and Compound 4 at 8 g ai/ha were also applied. These treatments were replicated two times. After treatment, the plants were maintained in a greenhouse and evaluated 19 days after spraying. All sprayed plants were evaluated for injury as compared to control plants that were sprayed only with non-phytotoxic solvent. Injury was evaluated visually using a 0 to 100% scale where 0 indicates no effect and 100 indicates complete control.

Results of Test B are shown in Table B, which lists the mean response of specific weeds to Compound 1, Compound 3 and Compound 4 applied alone as single active ingredients, the mean response of specific weeds to mixtures of Compound 1 and Compound 3, the expected additive effect of the herbicidal mixture of Compound 1 and Compound 3 (Colby's equation), the mean response of specific weeds to mixtures of Compound 1 and Compound 4, and the expected additive effect of the herbicidal mixture of Compound 1 and Compound 4 (Colby's equation). Weeds other than those specifically listed are also controlled by mixtures of Compound 1 and Compound 3, and by mixtures of Compound 1 and Compound 4. Different ratios of Compound 1 to Compound 3, and Compound 1 to Compound 4, and different formulation types, also provide useful weed control from the combination of the two herbicides.

TABLE B*

Effect of Compound 1, Compound 3 and Compound 4 as Active Ingredients Alone and in Mixture

| CMPD 1 | CMPD 3 | CMPD 4 | | TRZAS-R | TRZAS-E | AEGCY | BROTE | LOLMU | AVEFA |
|---|---|---|---|---|---|---|---|---|---|
| | Alone | | | | | | | | |
| 0 | 4 | 0 | Mean | 0 | 8 | 0 | 18 | 68 | 18 |
| 0 | 0 | 8 | Mean | 25 | 18 | 38 | 43 | 78 | 33 |
| 62 | 0 | 0 | Mean | 0 | 0 | 0 | 0 | 0 | 0 |
| 125 | 0 | 0 | Mean | 0 | 0 | 0 | 0 | 0 | 0 |
| 250 | 0 | 0 | Mean | 13 | 0 | 0 | 5 | 30 | 15 |
| 500 | 0 | 0 | Mean | 8 | 8 | 0 | 0 | 63 | 28 |
| | Mixtures | | | | | | | | |
| 62 | 4 | 0 | Mean | 10 | 0 | 25 | 28 | 73 | 28 |
| | | | Exp.† | 0 | 8 | 0 | 18 | 68 | 18 |
| 125 | 4 | 0 | Mean | 20 | 0 | 10 | 30 | 78 | 35 |
| | | | Exp. | 0 | 8 | 0 | 18 | 68 | 18 |
| 250 | 4 | 0 | Mean | 23 | 8 | 5 | 28 | 78 | 43 |
| | | | Exp. | 13 | 8 | 0 | 22 | 77 | 30 |
| 500 | 4 | 0 | Mean | 25 | 13 | 20 | 33 | 83 | 60 |
| | | | Exp. | 8 | 14 | 0 | 18 | 88 | 40 |
| 62 | 0 | 8 | Mean | 33 | 15 | 33 | 50 | 80 | 28 |
| | | | Exp. | 25 | 18 | 38 | 43 | 78 | 33 |
| 125 | 0 | 8 | Mean | 30 | 5 | 33 | 43 | 80 | 35 |
| | | | Exp. | 25 | 18 | 38 | 43 | 78 | 33 |
| 250 | 0 | 8 | Mean | 33 | 18 | 30 | 45 | 80 | 35 |
| | | | Exp. | 34 | 18 | 38 | 45 | 84 | 43 |
| 500 | 0 | 8 | Mean | 28 | 15 | 30 | 43 | 78 | 35 |
| | | | Exp. | 31 | 24 | 38 | 43 | 92 | 51 |

| CMPD 1 | CMPD 3 | CMPD 4 | | SETVI | KCHSC | APESV | PHAMI | ALOMY | POAAN |
|---|---|---|---|---|---|---|---|---|---|
| | Alone | | | | | | | | |
| 0 | 4 | 0 | Mean | 43 | 100 | 70 | 65 | 63 | 65 |
| 0 | 0 | 8 | Mean | 80 | 100 | 78 | 68 | 95 | 80 |
| 62 | 0 | 0 | Mean | 0 | 0 | 0 | 0 | 13 | 0 |
| 125 | 0 | 0 | Mean | 30 | 18 | 10 | 25 | 23 | 15 |
| 250 | 0 | 0 | Mean | 35 | 40 | 8 | 53 | 48 | 80 |
| 500 | 0 | 0 | Mean | 68 | 50 | 35 | 88 | 80 | 80 |

TABLE B*-continued

Effect of Compound 1, Compound 3 and Compound 4 as
Active Ingredients Alone and in Mixture

|     | Mixtures |   |       |    |     |     |    |     |     |
|-----|----------|---|-------|----|-----|-----|----|-----|-----|
| 62  | 4        | 0 | Mean  | 38 | 100 | 85  | 83 | 75  | 80  |
|     |          |   | Exp.† | 43 | 100 | 70  | 65 | 67  | 65  |
| 125 | 4        | 0 | Mean  | 78 | 100 | 90  | 78 | 80  | 85  |
|     |          |   | Exp.  | 60 | 100 | 73  | 74 | 71  | 70  |
| 250 | 4        | 0 | Mean  | 93 | 100 | 93  | 85 | 85  | 88  |
|     |          |   | Exp.  | 63 | 100 | 72  | 83 | 80  | 93  |
| 500 | 4        | 0 | Mean  | 88 | 100 | 100 | 90 | 85  | 98  |
|     |          |   | Exp.  | 81 | 100 | 81  | 96 | 93  | 93  |
| 62  | 0        | 8 | Mean  | 83 | 100 | 90  | 78 | 95  | 93  |
|     |          |   | Exp.  | 80 | 100 | 78  | 68 | 96  | 80  |
| 125 | 0        | 8 | Mean  | 80 | 100 | 95  | 85 | 98  | 95  |
|     |          |   | Exp.  | 86 | 100 | 80  | 76 | 96  | 83  |
| 250 | 0        | 8 | Mean  | 90 | 100 | 95  | 83 | 100 | 100 |
|     |          |   | Exp.  | 87 | 100 | 79  | 85 | 97  | 96  |
| 500 | 0        | 8 | Mean  | 98 | 100 | 100 | 83 | 100 | 100 |
|     |          |   | Exp.  | 94 | 100 | 85  | 96 | 99  | 96  |

*Rates are expressed in g ai/ha for Compound 1, Compound 3 and Compound 4. Data are reported as percent control.
†"Exp." are expected responses calculated according to Colby, S. R. "Calculating Synergistic and Antagonistic Responses of Herbicide Combinations," Weeds, 15(1), pp 20–22 (1967).

The following protocol was used for the test in Table C. Compound numbers are as described on page 28. The data demonstrate the efficacy of the Formula I and Formula IIi mixtures, the Formula I and Formula IIj mixtures, and the Formula I and Formula IIm mixtures of this invention against specific weeds. The weed control afforded by the mixtures of this invention are not limited, however, to these species.

Test C Protocol

*Triticum aestivum* cult. 'Recital' (TRZAS-R) (winter wheat), *Triticum aestivum* cult. 'Era' (TRZAS-E) (spring wheat), *Aegilops cylindrica* (AEGCY), *Bromus tectorum* (BROTE), *Avena fatua* (AVEFA), *Setaria viridis* (SETVI), *Apera spica-venti* (APESV), *Phalaris minor* (PHAMI), *Poa annua* (POAAN), an ordinary suceptible biotype of *Alopecurus myosuroides* (ALOMY-S), and a biotype of *Alopecurus myosuroides* (ALOMY-R) shown to be resistant to certain substituted urea, arylphenoxy, and cyclohexenone herbicides (Clarke, J. H; Moss, S. R. (1991) "The occurrence of herbicide-resistant *Alopecurus myosuroides* (black-grass) in the United Kingdom and strategies for its control" *Brighton Crop Protection Conference—Weeds*, 1041–1048) were grown in a greenhouse to approximately the two-leaf stage in 17-cm diameter round fiber pots filled with a mixture of 60% sandy loam soil and 40% Metro-Mix 350™ growing medium. Treatments were applied to the test species by diluting the compounds in a non-phytotoxic solvent, and spraying the treatments onto the plants. Compound 1 was applied at 500 g ai/ha. Compounds 5, 6 and 7 were each applied at 16 g ai/ha. Mixtures of Compound 1 at 500 g ai/ha and Compound 5 at 16 g ai/ha, Compound 1 at 500 g ai/ha and Compound 6 at 16 g ai/ha, and Compound 1 at 500 g ai/ha and Compound 7 at 16 g ai/ha were also applied. After treatment, the plants were maintained in a greenhouse and were evaluated 16 days after spraying. All sprayed plants were evaluated for injury as compared to control plants that were sprayed only with non-phytotoxic solvent. Injury was evaluated visually using a 0 to 100% scale where 0 indicates no effect and 100 indicates complete control.

Results of Test C are shown in Table C, which lists the observed response of specific weeds to Compound 1, Compound 5, Compound 6 and Compound 7 applied alone as single active ingredients, the observed response of specific weeds to mixtures of Compound 1 and Compound 5, the expected additive effect of the herbicidal mixture of Compounds 1 and Compound 5 (Colby's equation), the observed response of specific weeds to mixtures of Compound 1 and Compound 6, the expected additive effect of the herbicidal mixture of Compound 1 and Compound 6 (Colby's equation), the observed response of specific weeds to mixtures of Compound 1 and Compound 7, and the expected additive effect of the herbicidal mixture of Compound 1 and Compound 7 (Colby's equation). Weeds other than those specifically listed are also controlled by mixtures of Compound 1 and Compound 5, by mixtures of Compound 1 and Compound 6, and by mixtures of Compound 1 and Compound 7. Different ratios of Compound 1 to Compound 5, Compound 1 to Compound 6, and Compound 1 to Compound 7, and different formulation types, also provide useful weed control from the combination of the two herbicides.

TABLE C*

Effect of Compound 1, Compound 5, Compound 6 and Compound 7 as
Active Ingredients Alone and in Mixture

| CMPD 1 | CMPD 5 | CMPD 6 | CMPD 7 |       | TRZAS-R | TRZAS-E | AEGCY | BROTE | AVEFA | SETVI |
|--------|--------|--------|--------|-------|---------|---------|-------|-------|-------|-------|
|        |        | Alone  |        |       |         |         |       |       |       |       |
| 0      | 0      | 0      | 16     | Obs.† | 30      | 0       | 35    | 25    | 25    | 70    |
| 0      | 0      | 16     | 0      | Obs.  | 30      | 0       | 65    | 0     | 35    | 60    |

TABLE C*-continued

Effect of Compound 1, Compound 5, Compound 6 and Compound 7 as Active Ingredients Alone and in Mixture

| 0 | 16 | 0 | 0 | Obs. | 25 | 0 | 25 | 50 | 0 | 45 |
|---|---|---|---|---|---|---|---|---|---|---|
| 500 | 0 | 0 | 0 | Obs. | 0 | 0 | 10 | 0 | 0 | 40 |
| | | Mixtures | | | | | | | | |
| 500 | 16 | 0 | 0 | Obs. | 25 | 10 | 45 | 65 | 0 | 80 |
| | | | | Exp.† | 25 | 0 | 32 | 50 | 0 | 67 |
| 500 | 0 | 16 | 0 | Obs. | 35 | 25 | 65 | 30 | 65 | 85 |
| | | | | Exp. | 30 | 0 | 68 | 0 | 35 | 76 |
| 500 | 0 | 0 | 16 | Obs. | 30 | 15 | 45 | 60 | 40 | 85 |
| | | | | Exp. | 30 | 0 | 42 | 25 | 25 | 82 |

| CMPD 1 | CMPD 5 | CMPD 6 | CMPD 7 | | APESV | PHAMI | POAAN | ALOMY-S | ALOMY-R |
|---|---|---|---|---|---|---|---|---|---|
| | | Alone | | | | | | | |
| 0 | 0 | 0 | 16 | Obs.† | 40 | 65 | 65 | 50 | 10 |
| 0 | 0 | 16 | 0 | Obs. | 0 | 0 | 40 | 60 | 0 |
| 0 | 16 | 0 | 0 | Obs. | 80 | 40 | 60 | 65 | 0 |
| 500 | 0 | 0 | 0 | Obs. | 0 | 70 | 65 | 65 | 0 |
| | | Mixtures | | | | | | | |
| 500 | 16 | 0 | 0 | Obs. | 95 | 85 | 90 | 90 | 60 |
| | | | | Exp.† | 80 | 82 | 86 | 88 | 0 |
| 500 | 0 | 16 | 0 | Obs. | 90 | 85 | 90 | 85 | 35 |
| | | | | Exp. | 0 | 70 | 79 | 86 | 0 |
| 500 | 0 | 0 | 16 | Obs. | 90 | 90 | 85 | 80 | 40 |
| | | | | Exp. | 40 | 90 | 88 | 82 | 10 |

*Rates are expressed in g ai/ha for Compound 1, Compound 5, Compound 6 and Compound 7. Data are reported as percent control.
†"Obs." are the observed responses. "Exp." are expected responses calculated according to Colby, S. R. "Calculating Synergistic and Antagonistic Responses of Herbicide Combinations," Weeds, 15(1), pp 20–22 (1967).

The following protocol was used for the test in Table D. Compound numbers are as described on page 28. The data demonstrate the efficacy of the Formula I and Formula IIe mixtures of this invention against specific weeds. The weed control afforded by the mixtures of this invention are not limited, however, to these species.

Test D Protocol

*Triticum aestivum* cult. 'Recital' (TRZAS-R), *Triticum aestivum* cult. 'Era' (TRZAS-E), *Hordeum vulgare* cult. 'Igri' (HORVX), *Brassica napus* (BRSNN), *Avena fatua* (AVEFA), *Alopecurus myosuroides* (ALOMY), *Lolium multiflorum* (LOLMU), *Apera spica-venti* (APESV), *Galium aparine* (GALAP), *Polygonum convolvulus* (POLCO) and *Sinapis arvensis* (SINAR) were grown in a greenhouse to approximately the two-leaf stage in 15×20 cm rectangular fiber pots filled with a mixture of 60% sandy loam soil and 40% Metro-Mix 350™ growing medium. Treatments were applied to the test species by diluting the compounds in a non-phytotoxic solvent, and spraying the treatments onto the plants. Compound 1 was applied at 62 and 250 g ai/ha. Compound 8 was applied at 16 g ai/ha. Mixtures of Compound 1 at 62 g ai/ha and Compound 8 at 16 g ai/ha, and Compound 1 at 250 g ai/ha and Compound 8 at 16 g ai/ha were also applied. After treatment, the plants were maintained in a greenhouse and were evaluated 21 days after spraying. All sprayed plants were evaluated for injury as compared to control plants that were sprayed only with non-phytotoxic solvent. Injury was evaluated visually using a 0 to 100% scale where 0 indicates no effect and 100 indicates complete control.

Results of Test D are shown in Table D, which lists the observed response of specific weeds to Compound 1 and Compound 8 applied alone as single active ingredients, the observed responses of specific weeds to mixtures of Compound 1 and Compound 8, and the expected additive effect of the herbicidal mixtures of Compound 1 and Compound 8 (Colby's equation). Weeds other than those specifically listed are also controlled by mixtures of Compound 1 and Compound 8. Different ratios of Compound 1 to Compound 8, and different formulation types, also provide useful weed control from the combination of the two herbicides.

TABLE D*

Effect of Compound 1 and Compound 8 as Active Ingredients Alone and in Mixture

| CMPD 1 | CMPD 8 | | TRZAS-R | TRZAS-E | HORVX | BRSNN | AVEFA | ALOMY | LOLMU | APESV | GALAP | POLCO | SINAR |
|---|---|---|---|---|---|---|---|---|---|---|---|---|---|
| | Alone | | | | | | | | | | | | |
| 0 | 16 | Obs.† | 15 | 15 | 35 | 0 | 80 | 65 | 75 | 55 | 80 | 65 | 90 |
| 62 | 0 | Obs. | 10 | 0 | 20 | 15 | 0 | 0 | 0 | 0 | 40 | 20 | 20 |
| 250 | 0 | Obs. | 10 | 15 | 20 | 20 | 0 | 0 | 0 | 0 | 30 | 30 | 25 |

TABLE D*-continued

Effect of Compound 1 and Compound 8 as Active Ingredients Alone and in Mixture

| CMPD 1 | CMPD 8 | | TRZAS-R | TRZAS-E | HORVX | BRSNN | AVEFA | ALOMY | LOLMU | APESV | GALAP | POLCO | SINAR |
|---|---|---|---|---|---|---|---|---|---|---|---|---|---|
| Mixtures | | | | | | | | | | | | | |
| 62 | 16 | Obs. | 40 | 20 | 40 | 35 | 85 | 95 | 90 | 95 | 90 | 80 | 95 |
|  |  | Exp.† | 23 | 15 | 48 | 15 | 80 | 65 | 75 | 55 | 88 | 72 | 92 |
| 250 | 16 | Obs. | 55 | 35 | 45 | 35 | 90 | 90 | 90 | 98 | 98 | 80 | 95 |
|  |  | Exp. | 23 | 28 | 48 | 20 | 80 | 65 | 75 | 55 | 86 | 75 | 92 |

*Rates are expressed in g ai/ha for Compound 1 and Compound 8. Data are reported as percent control.
†"Obs." are the observed responses. "Exp." are expected responses calculated according to Colby, S. R. "Calculating Synergistic and Antagonistic Responses of Herbicide Combinations," Weeds, 15(1), pp 20–22 (1967).

The following protocol was used for the test in Table E. Compound numbers are as described on page 28. The data demonstrate the efficacy of the Formula I and Formula IIf mixtures and Formula I and Formula IIg mixtures of this invention against specific weeds. The weed control afforded by the mixtures of this invention are not limited, however, to these species.

Test E Protocol

*Zea mays* (corn, maize) cult. 'P3180' (ZEAMX-R), *Zea mays* cult. (corn, maize) 'P3180IR' (a commercial variety resistant to inhibitors of acetolactate synthase) (ZEAMX-E), *Gossypium hirsutum* (cotton) cult. 'Coker 312' (GOSHI), *Gossypium hirsutum* (cotton) cult. 'Coker 312—Transgenic' (a line derived from Coker 312 by inclusion of a gene conferring resistance to inhibitors of acetolactate synthase) (GOSHI-T), *Glycine max* (soybean) cult. 'Williams 82' (GLXMA), *Glycine max* (soybean) cult. 'W20' (a commercial variety resistant to inhibitors of acetolactate synthase) (GLXMA-W), *Brachiaria plantaginea* (BRAPL), *Echinochloa crus-galli* (ECHCG), *Digitaria sanguinalis* (DIGSA), *Cassia obtusifolia* (CASTO), *Abutilon theophrasti* (ABUTH) and *Solanum ptycanthum* (SOLPT) were grown in a greenhouse to the following approximate heights and leaf stages in 10-cm square pots containing sterilized sandy loam soil:

| Species | Application Height (cm) | Leaf Stage |
|---|---|---|
| *Zea mays* | 14 | 3 |
| *Gossypium hirsutum* | 7 | 1 |
| *Glycine max* | 7 | 1 trifoliate |
| *Brachiaria plantaginea* | 4 | 2–3 |
| *Echinochloa crus-galli* | 7 | 2–3 |
| *Digitaria sanguinalis* | 5 | 2–3 |
| *Cassia obtusifolia* | 4 | 1 |
| *Abutilon theophrasti* | 5 | 2–4 |
| *Solanum ptycanthum* | 1–4 | 2–4 |

Treatments were applied to the test species by diluting the compounds in a non-phytotoxic solvent containing a surfactant, and spraying the treatments onto the plants using a stationary laboratory circulating belt sprayer calibrated to deliver 280 L/ha though a single nozzle. Compound 1 was applied at 50, 100 and 200 g ai/ha. Compound 9 was applied at 2, 4 and 8 g ai/ha. Compound 10 was applied at 1, 2, and 4 g ai/ha. Mixtures of Compound 1 at 50, 100 and 200 g ai/ha with Compound 9 at 2, 4 and 8 g ai/ha, and Compound 1 at 50, 100 and 200 g ai/ha with Compound 10 at 1,2 and 4 g ai/ha were also applied. Individual treatments were replicated four times, with exception of *Solanum ptycanthum*, which was replicated once, and *Brachiaria plantaginea*, which was replicated three instead of four times for some application rates. Treatments were positioned in a greenhouse in a randomized complete block design. The greenhouse was maintained at a 28° C. average daily temperature, and natural light in the greenhouse was supplemented with artificial light to achieve a photoperiod of 14 hours. At 14 days after spraying, the plants were evaluated for injury as compared to control plants that were sprayed only with non-phytotoxic solvent. Injury was evaluated visually using a 0 to 100% scale where 0 indicates no effect and 100 indicates complete control.

Results of Test E are shown in Table E, which lists the observed response of specific weeds to Compound 1, Compound 9 and Compound 10 applied alone as single active ingredients, the observed responses of specific weeds to mixtures of Compound 1 and Compound 9 and of Compound 1 and Compound 10, and the expected additive effect of the herbicidal mixtures of Compound 1 and Compound 9 and of Compound 1 and Compound 10 (Colby's equation). Weeds other than those specifically listed are also controlled by mixtures of Compound 1 and Compound 9 and of Compound 1 and Compound 10. Different ratios of Compound 1 to Compound 9 and of Compound 1 to Compound 10, and different formulation types, also provide useful weed control from the combination of the two herbicides.

TABLE E*

Effect of Compound 1, Compound 9 and Compound 10 as Active Ingredients Alone and in Mixture

| CMPD 1 | CMPD 9 | CMPD 10 | | ZEAMX | ZEAMX-R | GOSHI | GOSHI-T | GLXMA | GLXMA-W | BRAPL | ECHCG | DIGSA | CASTO | ABUTH | SOLPT |
|---|---|---|---|---|---|---|---|---|---|---|---|---|---|---|---|
| Alone | | | | | | | | | | | | | | | |
| 50 | 0 | 0 | Mean | 20 | 12 | 0 | 0 | 0 | 0 | 0 | 0 | 0 | 0 | 0 | 0 |
| 100 | 0 | 0 | Mean | 15 | 12 | 15 | 2 | 8 | 5 | 3 | 8 | 2 | 0 | 0 | 0 |
| 200 | 0 | 0 | Mean | 22 | 18 | 25 | 18 | 18 | 18 | 10 | 35 | 15 | 0 | 0 | 0 |
| 0 | 2 | 0 | Mean | 18 | 12 | 5 | 5 | 0 | 0 | 27 | 28 | 0 | 0 | 0 | 0 |
| 0 | 4 | 0 | Mean | 18 | 15 | 48 | 2 | 5 | 2 | 73 | 58 | 5 | 0 | 5 | 0 |
| 0 | 8 | 0 | Mean | 20 | 15 | 58 | 5 | 10 | 5 | 83 | 58 | 30 | 20 | 28 | 20 |
| 0 | 0 | 1 | Mean | 18 | 12 | 30 | 2 | 72 | 12 | 20 | 65 | 20 | 28 | 18 | 0 |
| 0 | 0 | 2 | Mean | 12 | 15 | 58 | 8 | 82 | 38 | 50 | 88 | 40 | 55 | 55 | 0 |
| 0 | 0 | 4 | Mean | 15 | 12 | 72 | 10 | 92 | 55 | 57 | 100 | 42 | 78 | 70 | 10 |
| Mixtures | | | | | | | | | | | | | | | |
| 50 | 2 | 0 | Mean | 20 | 15 | 25 | 10 | 10 | 2 | 55 | 32 | 8 | 5 | 5 | 0 |
| | | | Exp.† | 34 | 23 | 5 | 5 | 0 | 0 | 27 | 28 | 0 | 0 | 0 | 0 |
| 100 | 2 | 0 | Mean | 15 | 15 | 40 | 18 | 5 | 5 | 60 | 48 | 8 | 0 | 0 | 0 |
| | | | Exp. | 30 | 23 | 19 | 7 | 8 | 5 | 29 | 34 | 2 | 0 | 2 | 0 |
| 200 | 2 | 0 | Mean | 15 | 15 | 50 | 18 | 18 | 15 | 70 | 52 | 30 | 2 | 0 | 0 |
| | | | Exp. | 36 | 28 | 29 | 22 | 18 | 18 | 34 | 53 | 15 | 0 | 10 | 0 |
| 50 | 4 | 0 | Mean | 18 | 12 | 50 | 12 | 5 | 5 | 82 | 58 | 20 | 0 | 0 | 0 |
| | | | Exp. | 34 | 25 | 48 | 2 | 5 | 2 | 73 | 58 | 5 | 0 | 12 | 0 |
| 100 | 4 | 0 | Mean | 12 | 10 | 68 | 15 | 15 | 15 | 88 | 82 | 22 | 10 | 5 | 0 |
| | | | Exp. | 30 | 25 | 56 | 4 | 13 | 7 | 74 | 62 | 7 | 0 | 35 | 0 |
| 200 | 4 | 0 | Mean | 25 | 12 | 70 | 25 | 20 | 18 | 77 | 6 | 32 | 20 | 5 | 40 |
| | | | Exp. | 36 | 30 | 61 | 20 | 22 | 20 | 76 | 80 | 19 | 0 | 45 | 0 |
| 50 | 8 | 0 | Mean | 20 | 15 | 68 | 15 | 30 | 15 | 100 | 73 | 40 | 28 | 50 | 50 |
| | | | Exp. | 36 | 25 | 58 | 5 | 10 | 5 | 83 | 92 | 30 | 20 | 5 | 20 |
| 100 | 8 | 0 | Mean | 12 | 10 | 72 | 20 | 40 | 20 | 83 | 58 | 50 | 35 | 28 | 60 |
| | | | Exp. | 32 | 25 | 64 | 7 | 17 | 10 | 90 | 95 | 31 | 20 | 52 | 20 |
| 200 | 8 | 0 | Mean | 12 | 12 | 70 | 32 | 35 | 22 | 84 | 61 | 52 | 55 | 28 | 60 |
| | | | Exp. | 38 | 30 | 68 | 22 | 26 | 22 | 97 | 100 | 40 | 55 | 58 | 20 |
| 50 | 0 | 1 | Mean | 12 | 10 | 60 | 10 | 80 | 48 | 85 | 73 | 32 | 20 | 28 | 0 |
| | | | Exp. | 34 | 23 | 30 | 2 | 72 | 12 | 53 | 62 | 20 | 25 | 32 | 0 |
| 100 | 0 | 1 | Mean | 20 | 12 | 48 | 10 | 72 | 25 | 20 | 65 | 25 | 28 | 18 | 0 |
| | | | Exp. | 30 | 23 | 40 | 4 | 74 | 16 | 47 | 75 | 22 | 40 | 48 | 0 |
| 200 | 0 | 1 | Mean | 15 | 12 | 40 | 15 | 85 | 40 | 50 | 68 | 22 | 28 | 18 | 20 |
| | | | Exp. | 36 | 28 | 62 | 20 | 77 | 28 | 28 | 77 | 42 | 48 | 52 | 0 |
| 50 | 0 | 2 | Mean | 15 | 12 | 70 | 18 | 88 | 42 | 60 | 82 | 32 | 28 | 72 | 10 |
| | | | Exp. | 30 | 25 | 58 | 8 | 82 | 38 | 50 | 88 | 40 | 65 | 55 | 0 |
| 100 | 0 | 2 | Mean | 20 | 12 | 58 | 15 | 82 | 38 | 50 | 88 | 40 | 55 | 80 | 10 |
| | | | Exp. | 25 | 25 | 70 | 10 | 85 | 50 | 70 | 98 | 48 | 60 | 55 | 0 |
| 200 | 0 | 2 | Mean | 10 | 12 | 64 | 20 | 83 | 41 | 52 | 89 | 41 | 55 | 55 | 10 |
| | | | Exp. | 31 | 30 | 78 | 20 | 90 | 55 | 78 | 100 | 55 | 45 | 70 | 10 |
| 50 | 0 | 4 | Mean | 18 | 18 | 68 | 25 | 85 | 49 | 55 | 92 | 49 | 55 | 55 | 0 |
| | | | Exp. | 32 | 23 | 72 | 18 | 90 | 58 | 78 | 100 | 62 | 88 | 88 | 20 |
| 100 | 0 | 4 | Mean | 15 | 12 | 92 | 18 | 90 | 55 | 88 | 100 | 80 | 78 | 70 | 20 |
| | | | Exp. | 28 | 23 | 76 | 12 | 93 | 57 | 58 | 100 | 43 | 78 | 70 | 10 |

TABLE E*-continued

Effect of Compound 1, Compound 9 and Compound 10 as Active Ingredients Alone and in Mixture

| CMPD 1 | CMPD 9 | CMPD 10 | | ZEAMX | ZEAMX-R | GOSHI | GOSHI-T | GLXMA | GLXMA-W | BRAPL | ECHCG | DIGSA | CASTO | ABUTH | SOLPT |
|---|---|---|---|---|---|---|---|---|---|---|---|---|---|---|---|
| 200 | 0 | 4 | Mean | 12 | 12 | 90 | 20 | 92 | 70 | 95 | 100 | 80 | 90 | 95 | 40 |
| | | | Exp. | 34 | 28 | 79 | 26 | 93 | 63 | 61 | 100 | 51 | 78 | 70 | 10 |

*Rates are expressed in g ai/ha for Compound 1, Compound 9 and Compound 10. Data are reported as percent control.
†"Exp." are expected responses calculated according to Colby, S. R. "Calculating Synergistic and Antagonistic Responses of Herbicide Combinations," Weeds, 15(1), pp 20–22 (1967).

The following protocol was used for the test in Table F. Compound numbers are as described on page 28. The data demonstrate the efficacy of the Formula I and Formula IIc mixtures and Formula I and Formula IIi mixtures of this invention against specific weeds. The weed control afforded by the mixtures of this invention ate not limited, however, to these species.

Test F Protocol

Zea mays (corn, maize) cult. 'P3180' (ZEAMX-R), Zea mays cult. (corn, maize) 'P3180IR' (a commercial variety resistant to inhibitors of acetolactate synthase) (ZEAMX-E), Glycine max (soybean) cult. 'Williams 82' (GLXMA), Glycine max (soybean) cult. 'W20' (a commercial variety resistant to inhibitors of acetolactate synthase) (GLXMA-W), Brachiaria plantaginea (BRAPL), Cassia obtusifolia (CASTO), Abutilon theophrasti (ABUTH) and Sida spinosa (SIDSP) were grown in a greenhouse to the following approximate heights and leaf stages in 10-cm square pots containing sterilized sandy loam soil:

| Species | Application | |
|---|---|---|
| | Height (cm) | Leaf Stage |
| Zea mays | 14 | 3 |
| Glycine max | 7 | 1 trifoliate |
| Brachiaria plantaginea | 4 | 2–3 |
| Cassia obtusifolia | 4 | 1 |
| Abutilon theophrasti | 5 | 2–4 |
| Sida spinosa | 2 | 1–2 |

Treatments were applied to the test species by diluting the compounds in a non-phytotoxic solvent containing a surfactant, and spraying the treatments onto the plants using a stationary laboratory circulating belt sprayer calibrated to deliver 280 L/ha through a single nozzle. Compound 1 was applied at 50, 100 and 200 g ai/ha. Compound 5 was applied at 1, 2 and 4 g ai/ha. Compound 11 was applied at 1, 2, and 4 g ai/ha. Mixtures of Compound 1 at 50, 100 and 200 g ai/ha with Compound 5 at 1, 2 and 4 g ai/ha, and Compound 1 at 50, 100 and 200 g ai/ha with Compound 11 at 1, 2 and 4 g ai/ha were also applied. Individual treatments were replicated four times, with exception of Compound 1 at 200 g ai/ha and Compound 5 at 1 g ai/ha, which was replicated three times. Treatments were positioned in a greenhouse in a randomized complete block design. The greenhouse was maintained at a 28° C. average daily temperature, and natural light in the greenhouse was supplemented with artificial light to achieve a photoperiod of 14 hours. At 14 days after spraying, the plants were evaluated for injury as compared to control plants that were sprayed only with non-phytotoxic solvent. Injury was evaluated visually using a 0 to 100% scale where 0 indicates no effect and 100 indicates complete control.

Results of Test F are shown in Table F, which lists the observed response of specific weeds to Compound 1, Compound 5 and Compound 11 applied alone as single active ingredients, the observed responses of specific weeds to mixtures of Compound 1 and Compound 5 and of Compound 1 and Compound 11, and the expected additive effect of the herbicidal mixtures of Compound 1 and Compound 5 and of Compound 1 and Compound 11 (Colby's equation). Weeds other than those specifically listed are also controlled by mixtures of Compound 1 and Compound 5 and of Compound 1 and Compound 11. Different ratios of Compound 1 to Compound 5 and of Compound 1 to Compound 11, and different formulation types, also provide useful weed control from the combination of the two herbicides.

TABLE F*

Effect of Compound 1, Compound 5 and Compound 11 as Active Ingredients Alone and in Mixture

| CMPD 1 | CMPD 5 | CMPD 11 | | ZEAMX | ZEAMX-R | GOSHI | GOSHI-T | GLXMA | GLXMA-W | BRAPL | CASTO | ABUTH | SIDSP |
|---|---|---|---|---|---|---|---|---|---|---|---|---|---|
| | Alone | | | | | | | | | | | | |
| 50 | 0 | 0 | Mean | 12 | 10 | 22 | 15 | 5 | 5 | 0 | 0 | 0 | 0 |
| 100 | 0 | 0 | Mean | 15 | 10 | 12 | 8 | 12 | 15 | 0 | 0 | 0 | 0 |
| 200 | 0 | 0 | Mean | 12 | 10 | 30 | 25 | 18 | 20 | 2 | 0 | 5 | 12 |
| 0 | 1 | 0 | Mean | 10 | 10 | 65 | 0 | 0 | 0 | 5 | 0 | 50 | 20 |
| 0 | 2 | 0 | Mean | 10 | 10 | 78 | 0 | 2 | 0 | 0 | 0 | 68 | 22 |
| 0 | 4 | 0 | Mean | 10 | 10 | 88 | 0 | 0 | 0 | 0 | 0 | 72 | 40 |
| 0 | 0 | 1 | Mean | 10 | 10 | 75 | 5 | 0 | 0 | 48 | 22 | 65 | 22 |
| 0 | 0 | 2 | Mean | 22 | 10 | 100 | 5 | 10 | 8 | 60 | 78 | 90 | 38 |
| 0 | 0 | 4 | Mean | 18 | 10 | 100 | 22 | 5 | 2 | 80 | 90 | 95 | 50 |
| | Mixtures | | | | | | | | | | | | |
| 50 | 1 | 0 | Mean | 10 | 10 | 80 | 20 | 8 | 10 | 0 | 0 | 60 | 25 |
| | | | Exp.† | 21 | 19 | 73 | 15 | 5 | 5 | 5 | 0 | 50 | 20 |
| 100 | 1 | 0 | Mean | 12 | 10 | 80 | 20 | 12 | 10 | 0 | 0 | 62 | 45 |
| | | | Exp. | 24 | 19 | 69 | 8 | 12 | 15 | 5 | 0 | 50 | 20 |
| 200 | 1 | 0 | Mean | 17 | 10 | 77 | 27 | 20 | 23 | 0 | 0 | 63 | 30 |
| | | | Exp. | 21 | 19 | 76 | 25 | 18 | 20 | 7 | 0 | 52 | 30 |
| 50 | 2 | 0 | Mean | 10 | 10 | 92 | 10 | 12 | 12 | 22 | 2 | 75 | 45 |
| | | | Exp. | 21 | 19 | 83 | 15 | 7 | 5 | 0 | 0 | 68 | 22 |
| 100 | 2 | 0 | Mean | 10 | 10 | 92 | 32 | 38 | 28 | 18 | 0 | 72 | 58 |
| | | | Exp. | 24 | 19 | 81 | 8 | 14 | 15 | 0 | 0 | 68 | 22 |
| 200 | 2 | 0 | Mean | 18 | 12 | 88 | 32 | 38 | 30 | 35 | 10 | 70 | 50 |
| | | | Exp. | 21 | 19 | 85 | 25 | 20 | 20 | 2 | 0 | 70 | 31 |
| 50 | 4 | 0 | Mean | 10 | 10 | 98 | 22 | 28 | 15 | 25 | 5 | 85 | 60 |
| | | | Exp. | 21 | 19 | 91 | 15 | 5 | 5 | 0 | 0 | 72 | 40 |
| 100 | 4 | 0 | Mean | 10 | 10 | 98 | 35 | 45 | 32 | 48 | 15 | 92 | 60 |
| | | | Exp. | 24 | 19 | 89 | 8 | 12 | 15 | 0 | 0 | 72 | 40 |
| 200 | 4 | 0 | Mean | 10 | 10 | 100 | 38 | 52 | 35 | 30 | 5 | 88 | 60 |
| | | | Exp. | 21 | 19 | 92 | 25 | 18 | 20 | 2 | 0 | 73 | 47 |

TABLE F*-continued

Effect of Compound 1, Compound 5 and Compound 11 as Active Ingredients Alone and in Mixture

| CMPD 1 | CMPD 5 | CMPD 11 | | ZEAMX | ZEAMX-R | GOSHI | GOSHI-T | GLXMA | GLXMA-W | BRAPL | CASTO | ABUTH | SIDSP |
|---|---|---|---|---|---|---|---|---|---|---|---|---|---|
| 50 | 0 | 1 | Mean | 10 | 10 | 80 | 20 | 0 | 0 | 60 | 60 | 82 | 38 |
|  |  |  | Exp. | 21 | 19 | 80 | 19 | 5 | 5 | 48 | 22 | 65 | 22 |
| 100 | 0 | 1 | Mean | 12 | 10 | 80 | 28 | 22 | 18 | 68 | 60 | 82 | 38 |
|  |  |  | Exp. | 24 | 19 | 78 | 13 | 12 | 15 | 48 | 22 | 65 | 22 |
| 200 | 0 | 1 | Mean | 18 | 10 | 92 | 32 | 12 | 15 | 80 | 75 | 82 | 38 |
|  |  |  | Exp. | 21 | 19 | 82 | 29 | 18 | 20 | 49 | 22 | 67 | 31 |
| 50 | 0 | 2 | Mean | 12 | 10 | 98 | 25 | 2 | 5 | 85 | 95 | 90 | 42 |
|  |  |  | Exp. | 31 | 19 | 100 | 19 | 14 | 13 | 60 | 78 | 90 | 38 |
| 100 | 0 | 2 | Mean | 12 | 10 | 98 | 32 | 18 | 20 | 85 | 88 | 90 | 38 |
|  |  |  | Exp. | 34 | 19 | 100 | 13 | 21 | 22 | 60 | 78 | 90 | 38 |
| 200 | 0 | 2 | Mean | 10 | 10 | 98 | 32 | 18 | 22 | 80 | 90 | 90 | 45 |
|  |  |  | Exp. | 31 | 19 | 100 | 29 | 26 | 26 | 61 | 78 | 90 | 45 |
| 50 | 0 | 4 | Mean | 25 | 10 | 100 | 30 | 15 | 15 | 85 | 98 | 92 | 42 |
|  |  |  | Exp. | 28 | 19 | 100 | 34 | 10 | 7 | 80 | 90 | 95 | 50 |
| 100 | 0 | 4 | Mean | 25 | 10 | 100 | 32 | 15 | 18 | 92 | 92 | 100 | 52 |
|  |  |  | Exp. | 30 | 19 | 100 | 28 | 16 | 17 | 80 | 90 | 95 | 50 |
| 200 | 0 | 4 | Mean | 25 | 10 | 100 | 35 | 18 | 18 | 88 | 95 | 100 | 62 |
|  |  |  | Exp. | 28 | 19 | 100 | 42 | 22 | 22 | 80 | 90 | 95 | 56 |

*Rates are expressed in g ai/ha for Compound 1, Compound 5, and Compound 11. Data are reported as percent control.
†"Exp." are expected responses calculated according to Colby, S. R. "Calculating Synergistic and Antagonistic Responses of Herbicide Combinations," Weeds, 15(1), pp 20–22 (1967).

The following protocol was used for the test in Table G. Compound numbers are as described on page 28. The data demonstrate the efficacy of mixtures of Formula I, Formula IIg and IIi against specific weeds. The weed control afforded by the mixtures of this invention are not limited, however, to these species.

Test G Protocol

Zea mays (corn, maize) cult. 'P3180' (ZEAMX-R), Zea mays cult. (corn, maize) 'P3180IR' (a commercial variety resistant to inhibitors of acetolactate synthase) (ZEAMX-E), Gossypium hirsutum (cotton) cult. 'Coker 312' ((GOSHI), Gossypium hirsutum (cotton) cult. 'Coker 312—Transgenic' (a line derived from Coker 312 by inclusion of a gene conferring resistance to inhibitors of acetolactate synthase) (GOSHI-T), Glycine max (soybean) cult. 'Williams 82' (GLXMA), Glycine max (soybean) cult. 'W20' (a commercial variety resistant to inhibitors of acetolactate synthase) (GLXMA-W), Brachiaria plantaginea (BRAPL), Echinochloa crus-galli (ECHCG) and Abutilon theophrasti (ABUTH) were grown in a greenhouse to the following approximate heights and leaf stages in 10-cm square pots containing sterilized sandy loam soil:

| Species | Application Height (cm) | Leaf Stage |
|---|---|---|
| Zea mays | 15 | 4 |
| Gossypium hirsutum | 13 | 2 |
| Glycine max | 10 | 1 trifoliate |
| Brachiaria plantaginea | 8 | 3 |
| Echinochloa crus-galli | 13 | 3 |
| Abutilon theophrasti | 7 | 4 |

Treatments were applied to the test species by diluting the formulated compounds in a non-phytotoxic solvent containing a surfactant, and spraying the treatments onto the plants using a stationary laboratory circulating belt sprayer calibrated to deliver 280 L/ha through a single nozzle. Compound 1 was applied at 50, 100 and 200 g ai/ha. Compound 5 and Compound 10 were applied in a 1:2 weight ratio totaling 1, 2 and 4 g ai/ha. Mixtures of Compound 1 at 50, 100 and 200 g ai/ha with a mixture of Compound 5 and Compound 10 in 1:2 weight ratio totaling 1, 2 and 4 g ai/ha were also applied. Individual treatments were replicated four times. Treatments were positioned in a greenhouse in a randomized complete block design. The greenhouse was maintained at a 28° C. average daily temperature, and natural light in the greenhouse was supplemented with artificial light to achieve a photoperiod of 14 hours. At 14 days after spraying, the plants were evaluated for injury as compared to control plants that were sprayed only with non-phytotoxic solvent. Injury was evaluated visually using a 0 to 100% scale where 0 indicates no effect and 100 indicates complete control.

Results of Test G are shown in Table G, which lists the observed response of specific weeds to Compound 1 and the 1:2 mixture of Compound 5 and Compound 10 applied alone as single active ingredients, the observed responses of specific weeds to mixtures of Compound 1 with the mixture of Compound 5 and Compound 10, and the expected additive effect of the herbicidal mixtures of Compound 1 with the mixture of Compound 5 and Compound 10 (Colby's equation). Weeds other than those specifically listed are also controlled by mixtures of Compound 1 with Compound 5 and Compound 10. Different ratios of Compound 1 to Compound 5 to Compound 10, and different formulation types, also provide useful weed control from the combination of the three herbicides.

TABLE G*

Effect of Compound 1, Compound 5 and Compound 10 as Active Ingredients Alone and in Mixture

| CMPD 1 | CMPD 5 | CMPD 10 | | ZEAMX | ZEAMX-R | GOSHI | GOSHI-T | GLXMA | GLXMA-W | BRAPL | ECHCG | ABUTH |
|---|---|---|---|---|---|---|---|---|---|---|---|---|
| Alone | | | | | | | | | | | | |
| 50 | 0 | 0 | Mean | 0 | 0 | 0 | 0 | 0 | 0 | 0 | 0 | 0 |
| 100 | 0 | 0 | Mean | 0 | 0 | 0 | 0 | 2 | 0 | 0 | 0 | 0 |
| 200 | 0 | 0 | Mean | 0 | 0 | 12 | 10 | 10 | 10 | 2 | 2 | 5 |
| 0 | 0.33 | 0.67 | Mean | 0 | 0 | 68 | 0 | 50 | 8 | 38 | 88 | 70 |
| 0 | 0.67 | 1.33 | Mean | 0 | 0 | 75 | 12 | 68 | 18 | 60 | 92 | 90 |
| 0 | 1.33 | 2.67 | Mean | 0 | 0 | 88 | 30 | 88 | 50 | 90 | 100 | 98 |
| Mixtures | | | | | | | | | | | | |
| 50 | 0.33 | 0.67 | Mean | 0 | 0 | 78 | 10 | 52 | 18 | 50 | 92 | 90 |
| | | | Exp.† | 0 | 0 | 68 | 0 | 50 | 8 | 38 | 88 | 70 |
| 100 | 0.33 | 0.67 | Mean | 0 | 0 | 80 | 22 | 48 | 22 | 58 | 95 | 88 |
| | | | Exp. | 0 | 0 | 68 | 0 | 51 | 8 | 38 | 88 | 70 |
| 200 | 0.33 | 0.67 | Mean | 0 | 0 | 78 | 28 | 50 | 25 | 62 | 90 | 85 |
| | | | Exp. | 0 | 0 | 72 | 10 | 55 | 17 | 39 | 88 | 72 |
| 50 | 0.67 | 1.33 | Mean | 0 | 0 | 82 | 30 | 75 | 45 | 82 | 100 | 90 |
| | | | Exp. | 0 | 0 | 75 | 12 | 68 | 18 | 60 | 92 | 90 |
| 100 | 0.67 | 1.33 | Mean | 0 | 0 | 85 | 32 | 75 | 32 | 82 | 100 | 95 |
| | | | Exp. | 0 | 0 | 75 | 12 | 69 | 18 | 60 | 92 | 90 |
| 200 | 0.67 | 1.33 | Mean | 0 | 0 | 82 | 38 | 82 | 42 | 90 | 98 | 100 |
| | | | Exp. | 0 | 0 | 78 | 21 | 71 | 26 | 61 | 92 | 90 |
| 50 | 1.33 | 2.67 | Mean | 0 | 0 | 88 | 45 | 88 | 50 | 92 | 100 | 100 |
| | | | Exp. | 0 | 0 | 88 | 30 | 88 | 50 | 90 | 100 | 98 |
| 100 | 1.33 | 2.67 | Mean | 0 | 0 | 88 | 50 | 88 | 55 | 95 | 100 | 98 |
| | | | Exp. | 0 | 0 | 88 | 30 | 88 | 50 | 90 | 100 | 98 |
| 200 | 1.33 | 2.67 | Mean | 0 | 0 | 85 | 52 | 90 | 52 | 95 | 98 | 100 |
| | | | Exp. | 0 | 0 | 89 | 37 | 89 | 55 | 90 | 100 | 98 |

*Rates are expressed in g ai/ha for Compound 1, Compound 5 and Compound 10. Data are reported as percent control.
†"Exp." are expected responses calculated according to Colby, S. R. "Calculating Synergistic and Antagonistic Responses of Herbicide Combinations," Weeds, 15(1), pp 20–22 (1967).

The following protocol was used for the test in Table H. Compound numbers are as described on page 28. The data demonstrate the efficacy of mixtures of Formula I, Formula IIc and IIf against specific weeds. The weed control afforded by the mixtures of this invention are not limited, however, to these species.

Test H Protocol

Zea mays (Corn, maize) cult. 'P3180' (ZEAMX-R), Zea mays cult. (corn, maize) 'P3180IR' (a commercial variety resistant to inhibitors of acetolactate synthase) (ZEAMX-E), Gossypium hirsutum (cotton) cult. 'Coker 312' (GOSHI), Gossypium hirsutum (cotton) cult. 'Coker 312—Transgenic' (a line derived from Coker 312 by inclusion of a gene conferring resistance to inhibitors of acetolactate synthase) (GOSHI-T), Glycine max (soybean) cult. 'Williams 82' (GLXMA), Glycine max (soybean) cult. 'W20' (a commercial variety resistant to inhibitors of acetolactate synthase) (GLXMA-W), Brachiaria plantaginea (BRAPL) and Echinochloa crus-galli (ECHCG) were grown in a greenhouse to the following approximate heights and leaf stages in 10-cm square pots containing sterilized sandy loren soil:

| Species | Application | |
|---|---|---|
| | Height (cm) | Leaf Stage |
| Zea mays | 18 | 3 |
| Gossypium hirsutum | 15 | 2 |
| Glycine max | 12 | 1 trifoliate |
| Brachiaria plantaginea | 6 | 2 |
| Echinochloa crus-galli | 14 | 3 |

Treatments were applied to the test species by diluting the formulated compounds in a non-phytotoxic solvent containing a surfactant, and spraying the treatments onto the plants using a stationary laboratory circulating belt sprayer calibrated to deliver 280 L/ha through a single nozzle. Compound 1 was applied at 50, 100 and 200 g ai/ha. Compound 9 and Compound 11 were applied in a 1:1 weight ratio totaling 2 and 4 g ai/ha. Mixtures of Compound 1 at 50, 100 and 200 g ai/ha with a mixture of Compound 9 and Compound 11 in 1:1 weight ratio totaling 2 and 4 g ai/ha were also applied. Individual treatments were replicated four times. Treatments were positioned in a greenhouse in a randomized complete block design. The greenhouse was maintained at a 28° C. average daily temperature, and natural light in the greenhouse was supplemented with artificial light to achieve a photoperiod of 14 hours. At 14 days after spraying, the plants were evaluated for injury as compared to control plants that were sprayed only with non-phytotoxic solvent. Injury was evaluated visually using a 0 to 100% scale where 0 indicates no effect and 100 indicates complete control.

Results of Test H are shown in Table H, which lists the observed response of specific weeds to Compound 1 as a single active ingredient and Compound 9 and Compound 11 mixed together without Compound 1, the observed responses of specific weeds to mixtures of Compound 1 with the mixture of Compound 9 and Compound 11, and the expected additive effect of the herbicidal mixtures of Compound 1 with the mixture of Compound 9 and Compound 11 (Colby's equation). Weeds other than those specifically listed are also controlled by mixtures of Compound 1 with Compound 9 and Compound 11. Different ratios of Compound 1 to Compound 9 to Compound 11, and different formulation types, also provide useful weed control from the combination of the three herbicides.

TABLE H*

Effect of Compound 1, Compound 9 and Compound 11
as Active Ingredients Alone and in Mixture

| CMPD 1 | CMPD 9 | CMPD 11 | | ZEAMX | ZEAMX-R | GOSHI | GOSHI-T | GLXMA | GLXMA-W | BRAPL | ECHCG |
|---|---|---|---|---|---|---|---|---|---|---|---|
| | Alone | | | | | | | | | | |
| 50 | 0 | 0 | Mean | 0 | 0 | 12 | 5 | 2 | 0 | 0 | 0 |
| 100 | 0 | 0 | Mean | 0 | 0 | 40 | 28 | 10 | 12 | 0 | 0 |
| 200 | 0 | 0 | Mean | 0 | 0 | 50 | 30 | 5 | 10 | 15 | 10 |
| 0 | 1 | 1 | Mean | 0 | 0 | 68 | 2 | 0 | 0 | 35 | 42 |
| 0 | 2 | 2 | Mean | 0 | 0 | 82 | 10 | 2 | 2 | 55 | 88 |
| | Mixtures | | | | | | | | | | |
| 50 | 1 | 1 | Mean | 0 | 0 | 65 | 18 | 2 | 5 | 40 | 58 |
| | | | Exp. | 0 | 0 | 72 | 7 | 2 | 0 | 35 | 42 |
| 100 | 1 | 1 | Mean | 0 | 0 | 58 | 18 | 5 | 5 | 55 | 55 |
| | | | Exp. | 0 | 0 | 81 | 29 | 10 | 12 | 35 | 42 |
| 200 | 1 | 1 | Mean | 0 | 0 | 80 | 32 | 8 | 12 | 60 | 72 |
| | | | Exp. | 0 | 0 | 84 | 31 | 5 | 10 | 45 | 48 |
| 50 | 2 | 2 | Mean | 0 | 0 | 80 | 25 | 2 | 0 | 68 | 92 |
| | | | Exp. | 0 | 0 | 84 | 14 | 4 | 2 | 55 | 88 |
| 100 | 2 | 2 | Mean | 0 | 0 | 88 | 32 | 10 | 8 | 75 | 92 |
| | | | Exp. | 0 | 0 | 89 | 35 | 12 | 14 | 55 | 88 |
| 200 | 2 | 2 | Mean | 0 | 0 | 82 | 48 | 5 | 12 | 85 | 95 |
| | | | Exp. | 0 | 0 | 91 | 37 | 7 | 12 | 62 | 89 |

*Rates are expressed in g ai/ha for Compound 1, Compound 9 and Compound 11. Data are reported as percent control.
†"Exp." are expected responses calculated according to Colby, S. R. "Calculating Synergistic and Antagonistic Responses of Herbicide Combinations," Weeds, 15(1), pp 20–22 (1967).

The following protocol was used for the test in Table I. Compound numbers are as described on page 28. The data demonstrate the efficacy of the Formula I and Formula IIk mixtures of this invention against specific weeds. The weed control afforded by the mixtures of this invention are not limited, however, to these species.

Test I Protocol

*Beta vulgaris* (BEAVA), *Avena fatua* (AVEFA), *Lolium multiflorum* (LOLMU), *Apera spica-venti* (APESV), *Bromus tectorium* (BROTE) and *Sinapis arvensis* (SINAR) were grown in a greenhouse to approximately the two-leaf stage in 15×20 cm rectangular fiber pots filled with a mixture of 60% sandy loam soil and 40% Metro-Mix 350™ growing medium. Treatments were applied to the test species by diluting the compounds in a non-phytotoxic solvent, and spraying the treatments onto the plants. Compound 1 was applied at 8 and 16 g ai/ha. Compound 12 was applied at 16 g ai/ha. Mixtures of Compound 1 at 8 g ai/ha and Compound 12 at 16 g ai/ha, and Compound 1 at 16 g ai/ha and Compound 12 at 16 g ai/ha were also applied. After treatment, the plants were maintained in a greenhouse and were evaluated 14 days after spraying. All sprayed plants were evaluated for injury as compared to control plants that were sprayed only with non-phytotoxic solvent. Injury was evaluated visually using a 0 to 100% scale where 0 indicates no effect and 100 indicates complete control.

Results of Test I are shown in Table I, which lists the observed response of specific weeds to Compound 1 and Compound 12 applied alone as single active ingredients, the observed responses of specific weeds to mixtures of Compound 1 and Compound 12, and the expected additive effect of the herbicidal mixtures of Compound 1 and Compound 12 (Colby's equation). Weeds other than those specifically listed are also controlled by mixtures of Compound 1 and Compound 12. Different ratios of Compound 1 to Compound 12, and different formulation types, also provide useful weed control from the combination of the two herbicides.

TABLE I*

Effect of Compound 1 and Compound 12
as Active Ingredients Alone and in Mixture

| CMPD 1 | CMPD 12 | | BEAVA | SINAR | AVEFA | BROTE | LOLMU | APESV |
|---|---|---|---|---|---|---|---|---|
| | Alone | | | | | | | |
| 0 | 16 | Obs. | 0 | 90 | 55 | 35 | 0 | 65 |
| 8 | 0 | Obs.† | 0 | 0 | 0 | 0 | 0 | 0 |
| 16 | 0 | Obs. | 0 | 0 | 0 | 0 | 0 | 25 |
| | Mixtures | | | | | | | |
| 8 | 16 | Obs. | 25 | 95 | 60 | 50 | 60 | 70 |
| | | Exp.† | 0 | 90 | 55 | 35 | 0 | 65 |
| 16 | 16 | Obs. | 0 | 100 | 60 | 55 | 50 | 80 |
| | | Exp. | 0 | 90 | 55 | 35 | 0 | 74 |

TABLE I*-continued

Effect of Compound 1 and Compound 12 as Active Ingredients Alone and in Mixture

| CMPD 1 | CMPD 12 | BEAVA | SINAR | AVEFA | BROTE | LOLMU | APESV |
|---|---|---|---|---|---|---|---|

*Rates are expressed in g ai/ha for Compound 1 and Compound 12. Data are reported as percent control.
†"Obs." are the observed responses. "Exp." are expected responses calculated according to Colby, S. R. "Calculating Synergistic and Antagonistic Responses of Herbicide Combinations," Weeds, 15(1), pp 20–22 (1967).

The following protocol was used for the test in Table J. Compound numbers are as described on page 28. The data demonstrate the efficacy of the Formula I and Formula IIn mixtures of this invention against a specific weed. The weed control afforded by the mixtures of this invention are not limited, however, to this species.

Test J Protocol

Plastic pots were partially filled with silt loam soil. The soil was then flooded with water, and seeds of barnyardgrass (*Echinochloa crus-galli*) were planted in saturated soil, and the plants grown to the 2-leaf stage for testing. At treatment time, the water level for all plantings was raised to 2 cm above the soil surface. Chemical treatments were formulated in a non-phytotoxic solvent mixture containing a surfactant and applied directly to the paddy water. These treatments were replicated twice. Treated plants and controls were maintained in a greenhouse for 21 days, after which time all species were compared to controls and visually evaluated. Plant response ratings, summarized in Table J are reported on a 0 to 100 scale where 0 is no effect and 100 is complete control.

Results of Test J are shown in Table J, which lists the mean response of a specific weed to Compound 1 and Compound 13 applied alone as single active ingredients, applied as a mixture of Compound 1 and Compound 13, and the expected additive effect of the herbicidal mixture of Compound 1 and Compound 13 (from Colby's equation). Weeds other than those specifically listed are also controlled by mixtures of Compound 1 and Compound 13. Different ratios of Compound 1 to Compound 13, and different formulation types, also provide useful weed control from the combination of the two herbicides.

TABLE J*

Effect of Compound 1 and Compound 13 as Active Ingredients Alone and in Mixture

| Compound 1 | Compound 13 | Barnyardgrass (2 L.S.) | |
|---|---|---|---|
| | | Mean | Expected† |
| Alone | | | |
| 100 | 0 | 28 | — |
| 200 | 0 | 22 | — |
| 400 | 0 | 90 | — |
| 0 | 250 | 25 | — |
| 0 | 500 | 25 | — |
| 0 | 1000 | 42 | — |
| 0 | 2000 | 72 | — |
| 0 | 4000 | 62 | — |
| Mixtures | | | |
| 100 | 250 | 72 | 46 |
| 200 | 250 | 80 | 42 |
| 400 | 250 | 95 | 92 |
| 100 | 500 | 88 | 46 |

TABLE J*-continued

Effect of Compound 1 and Compound 13 as Active Ingredients Alone and in Mixture

| Compound 1 | Compound 13 | Barnyardgrass (2 L.S.) | |
|---|---|---|---|
| | | Mean | Expected† |
| 200 | 500 | 88 | 42 |
| 400 | 500 | 95 | 92 |
| 100 | 1000 | 70 | 58 |
| 200 | 1000 | 80 | 55 |
| 400 | 1000 | 92 | 94 |
| 100 | 2000 | 85 | 80 |
| 200 | 2000 | 98 | 78 |
| 400 | 2000 | 100 | 97 |
| 100 | 4000 | 98 | 73 |
| 200 | 4000 | 98 | 70 |
| 400 | 4000 | 100 | 96 |

*Application rates are expressed in g ai/ha for both Compound 1 and Compound 13. Data are reported as percent control.
†Colby, S. R. "Calculating Synergistic and Antagonistic Responses of Herbicide Combinations," Weeds, 15(1); pp 20–22 (1967).

The following protocol was used for the test in Table K. Compound numbers are as described on page 28. The data demonstrate the efficacy of the Formula I and Formula IIn mixtures of this invention against a specific weed. The weed control afforded by the mixtures of this invention are not limited, however, to this species.

Test K Protocol

Plastic pots were partially filled with silt loam soil. The soil was then flooded with water, and seeds of a biotype of barnyardgrass (*Echinochloa crus-galli*) resistant to the compound of Formula IIn were planted in saturated soil, and the plants grown to the 2-leaf stage for testing. At treatment time, the water level for all plantings was raised to 2 cm above the soil surface. Chemical treatments were formulated in a non-phytotoxic solvent mixture containing a surfactant and applied directly to the paddy water. These treatments were replicated twice. Treated plants and controls were maintained in a greenhouse for 21 days, after which time all species were compared to controls and visually evaluated. Plant response ratings, summarized in Table K are reported on a 0 to 100 scale where 0 is no effect and 100 is complete control.

Results of Test K are shown in Table K, which lists the mean response of a specific weed to Compound 1 and Compound 13 applied alone as single active ingredients, applied as a mixture of Compound 1 and Compound 13, and the expected additive effect of the herbicidal mixture of Compound 1 and Compound 13 (from Colby's equation). Weeds other than those specifically listed are also controlled by mixtures of Compound 1 and Compound 13. Different ratios of Compound 1 to Compound 13, and different formulation types, also provide useful weed control from the combination of the two herbicides.

TABLE K*

Effect of Compound 1 and Compound 13 as Active Ingredients Alone and in Mixture

| Compound 1 | Compound 13 | Resistant Barnyardgrass (2 L.S.) Mean | Expected† |
|---|---|---|---|
| Alone | | | |
| 25 | 0 | 0 | — |
| 50 | 0 | 0 | — |
| 100 | 0 | 18 | — |
| 200 | 0 | 60 | — |
| 400 | 0 | 70 | — |
| 0 | 250 | 12 | — |
| 0 | 500 | 8 | — |
| 0 | 1000 | 20 | — |
| 0 | 2000 | 22 | — |
| 0 | 4000 | 38 | — |
| Mixtures | | | |
| 25 | 250 | 15 | 12 |
| 50 | 250 | 25 | 12 |
| 100 | 250 | 50 | 28 |
| 400 | 250 | 88 | 74 |
| 25 | 500 | 28 | 8 |
| 50 | 500 | 30 | 8 |
| 100 | 500 | 30 | 25 |
| 200 | 500 | 68 | 63 |
| 400 | 500 | 82 | 72 |
| 50 | 1000 | 22 | 20 |
| 400 | 1000 | 96 | 76 |
| 25 | 2000 | 50 | 22 |
| 50 | 2000 | 48 | 22 |
| 100 | 2000 | 50 | 36 |
| 400 | 2000 | 96 | 77 |
| 25 | 4000 | 50 | 38 |
| 50 | 4000 | 52 | 38 |
| 100 | 4000 | 68 | 49 |
| 200 | 4000 | 96 | 75 |
| 400 | 4000 | 100 | 81 |

*Application rates are expressed in g ai/ha for both Compound 1 and Compound 13. Data are reported as percent control.
†Colby, S. R. "Calculating Synergistic and Antagonistic Responses of Herbicide Combinations," Weeds, 15(1); pp 20–22 (1967).

The following protocol was used for the test in Table L. Compound numbers are as described on page 28. The data demonstrate the efficacy of the Formula I and Formula IIb mixtures of this invention against a specific weed. The weed control afforded by the mixtures of this invention are not limited, however, to this species.

Test L Protocol

Plastic pots were partially filled with silt loam soil, and seed of ducksalad (*Heteranthera limosa*) were added interspersed in soil to form a 1-cm-thick top layer. The soil was then flooded with water, and the plants grown to the 2-leaf stage for testing. At treatment time, the water level for all plantings was raised to 3 cm above the soil surface. Chemical treatments were formulated in a non-phytotoxic solvent mixture containing a surfactant and applied directly to the paddy water. These treatments were replicated twice. Treated plants and controls were maintained in a greenhouse for 21 days, after which time all species were compared to controls and visually evaluated. Plant response ratings, summarized in Table L are reported on a 0 to 100 scale where 0 is no effect and 100 is complete control.

Results of Test L are shown in Table L, which lists the mean response of a specific weed to Compound 1 and Compound 3 applied alone as single active ingredients, applied as a mixture of Compound 1 and Compound 3, and the expected additive effect of the herbicidal mixture of Compound 1 and Compound 3 (from Colby's equation).

Weeds other than those specifically listed are also controlled by mixtures of Compound 1 and Compound 3. Different ratios of Compound 1 to Compound 3, and different formulation types, also provide useful weed control from the combination of the two herbicides.

TABLE L*

Effect of Compound 1 and Compound 3 as Active Ingredients Alone and in Mixture

| Compound 1 | Compound 3 | Ducksalad (2 L.S.) Mean | Expected† |
|---|---|---|---|
| Alone | | | |
| 25 | 0 | 10 | — |
| 50 | 0 | 20 | — |
| 75 | 0 | 0 | — |
| 0 | 0.5 | 28 | — |
| 0 | 1 | 88 | — |
| 0 | 2 | 90 | — |
| 0 | 3 | 95 | — |
| 0 | 4 | 100 | — |
| Mixtures | | | |
| 25 | 0.5 | 55 | 35 |
| 25 | 1 | 95 | 89 |
| 25 | 2 | 92 | 91 |
| 25 | 3 | 98 | 96 |
| 25 | 4 | 98 | 100 |
| 50 | 0.5 | 70 | 42 |
| 50 | 1 | 90 | 90 |
| 50 | 2 | 98 | 92 |
| 50 | 3 | 100 | 96 |
| 50 | 4 | 100 | 100 |
| 75 | 0.5 | 85 | 28 |
| 75 | 1 | 98 | 88 |
| 75 | 2 | 100 | 90 |
| 75 | 3 | 100 | 95 |
| 75 | 4 | 100 | 100 |

*Application rates are expressed in g ai/ha for both Compound 1 and Compound 3. Data are reported as percent control.
†Colby, S. R. "Calculating Synergistic and Antagonistic Responses of Herbicide Combinations," Weeds, 15(1); pp 20–22 (1967).

The following protocol was used for the test in Table M. Compound numbers are as described on page 28. The data demonstrate the efficacy of the Formula I and Formula IIh mixtures of this invention against specific weeds. The weed control afforded by the mixtures of this invention are not limited, however, to these species.

Test M Protocol 10-cm square plastic pots were partially filled with sandy loam soil and planted with seeds of barnyardgrass (*Echinochloa crus-galli*) and wild mustard (*Sinapis arvensis*), which were covered with 0.5 cm of soil. Treatments were applied by diluting the compounds in a non-phytotoxic solvent containing a surfactant and then spraying the treatments onto the soil surface using a stationary laboratory circulating belt sprayer calibrated to deliver 327 L/ha through a single nozzle. Compound 1 was applied at 64 and 125 g ai/ha. Compound 14 was applied at 0.25, 0.5, 1, 2, 4, 8 and 16 g ai/ha. Mixtures of Compound 1 at 64 and 125 g ai/ha and Compound 14 at 0.25, 0.5, 1, 2, 4, 8 and 16 g ai/ha were also applied. Individual treatments were replicated three times. Treatments were positioned in a greenhouse in a randomized complete block design. The greenhouse was maintained at a 28° C. average daily temperature, and natural light in the greenhouse was supplemented with artificial light to achieve a photoperiod of 14 hours. At 26 days after spraying, the plants were evaluated for injury as compared to control plants that were sprayed only with non-phytotoxic solvent. Injury was evaluated visually using a 0 to 100% scale where 0 indicates no effect and 100 indicates complete control.

Results of Test M are shown in Table M, which lists the observed response of specific weeds to Compound 1 and Compound 14 applied alone as single active ingredients, the observed responses of specific weeds to mixtures of Compound 1 and Compound 14, and the expected additive effect of the herbicidal mixtures of Compound 1 and Compound 14 (Colby's equation). Weeds other than those specifically listed are also controlled by mixtures of Compound 1 and Compound 14. Different ratios of Compound 1 to Compound 14, and different formulation types, also provide useful weed control from the combination of the two herbicides.

TABLE M*

Effect of Compound 1 and Compound 14
as Active Ingredients Alone and in Mixture

| Compound 1 | Compound 14 | Barnyardgrass Mean | Expected† | Wild Mustard Mean | Expected |
|---|---|---|---|---|---|
| Alone | | | | | |
| 64 | 0 | 3 | — | 23 | — |
| 125 | 0 | 62 | — | 38 | — |
| 0 | 0.25 | 7 | — | 83 | — |
| 0 | 0.5 | 12 | — | 95 | — |
| 0 | 1 | 67 | — | 98 | — |
| 0 | 2 | 92 | — | 95 | — |
| 0 | 4 | 92 | — | 99 | — |
| 0 | 8 | 99 | — | 99 | — |
| 0 | 16 | 100 | — | 100 | — |
| Mixtures | | | | | |
| 64 | 0.25 | 35 | 10 | 95 | 87 |
| 64 | 0.5 | 68 | 15 | 97 | 96 |
| 64 | 1 | 76 | 68 | 99 | 98 |
| 64 | 2 | 99 | 92 | 99 | 96 |
| 64 | 4 | 100 | 92 | 99 | 99 |
| 64 | 8 | 100 | 99 | 99 | 99 |
| 64 | 16 | 100 | 100 | 100 | 100 |
| 125 | 0.25 | 68 | 65 | 98 | 89 |
| 125 | 0.5 | 80 | 67 | 97 | 97 |
| 125 | 1 | 86 | 87 | 98 | 99 |
| 125 | 2 | 100 | 97 | 99 | 97 |
| 125 | 4 | 99 | 97 | 100 | 99 |
| 125 | 8 | 99 | 100 | 99 | 99 |
| 125 | 16 | 100 | 100 | 100 | 100 |

*Rates are expressed in g ai/ha for Compound 1 and Compound 14. Data are reported as percent control.
†"Expected" are expected responses calculated according to Colby, S. R. "Calculating Synergistic and Antagonistic Responses of Herbicide Combinations," Weeds, 15(1), pp 20–22 (1967).

The following protocol was used for the test in Table N. Compound numbers are as described on page 28. The data demonstrate the efficacy of the Formula I and Formula IIo mixtures of this invention against specific weeds. The weed control afforded by the mixtures of this invention are not limited, however, to these species.

Test N Protocol 10-cm square plastic pots were partially filled with sandy loam soil and then planted with seeds of guineagrass (*Panicum maximum*) and large crabgrass (*Digitara sanguinalis*), which were covered with 0.5 cm of soil. Treatments were applied by diluting the compounds in a non-phytotoxic solvent containing a surfactant and then spraying the treatments onto the soil surface using a stationary laboratory circulating belt sprayer calibrated to deliver 327 L/ha through a single nozzle. Compound 1 was applied at 64, 125 and 250 g ai/ha. Compound 15 was applied at 16, 32, 64 and 125 g ai/ha. Mixtures of Compound 1 at 64, 125 and 250 g ai/ha and Compound 15 at 16, 32, 64 and 125 g ai/ha were also applied. Individual treatments were replicated three times. Treatments were positioned in a greenhouse in a randomized complete block design. The greenhouse was maintained at a 28° C. average daily temperature, and natural light in the greenhouse was supplemented with artificial light to achieve a photoperiod of 14 hours. At 22 days after spraying, the plants were evaluated for injury as compared to control plants that were sprayed only with non-phytotoxic solvent. Injury was evaluated visually using a 0 to 100% scale where 0 indicates no effect and 100 indicates complete control.

Results of Test N are shown in Table N, which lists the observed response of specific weeds to Compound 1 and Compound 15 applied alone as single active ingredients, the observed responses of specific weeds to mixtures of Compound 1 and Compound 15, and the expected additive effect of the herbicidal mixtures of Compound 1 and Compound 15 (Colby's equation). Weeds other than those specifically listed are also controlled by mixtures of Compound 1 and Compound 15. Different ratios of Compound 1 to Compound 15, and different formulation types, also provide useful weed control from the combination of the two herbicides.

TABLE N*

Effect of Compound 1 and Compound 15
as Active Ingredients Alone and in Mixture

| Compound 1 | Compound 15 | Guineagrass Mean | Expected† | Large Crabgrass Mean | Expected |
|---|---|---|---|---|---|
| Alone | | | | | |
| 64 | 0 | 30 | — | 2 | — |
| 125 | 0 | 60 | — | 80 | — |
| 250 | 0 | 98 | — | 96 | — |
| 0 | 16 | 0 | — | 15 | — |
| 0 | 32 | 0 | — | 74 | — |
| 0 | 64 | 39 | — | 96 | — |
| 0 | 125 | 85 | — | 98 | — |
| Mixtures | | | | | |
| 64 | 16 | 52 | 30 | 42 | 17 |
| 64 | 32 | 38 | 30 | 76 | 75 |
| 64 | 64 | 80 | 57 | 100 | 96 |
| 64 | 125 | 95 | 90 | 100 | 98 |
| 125 | 16 | 86 | 60 | 84 | 83 |
| 125 | 32 | 81 | 60 | 100 | 95 |
| 125 | 64 | 94 | 76 | 100 | 99 |
| 125 | 125 | 98 | 94 | 100 | 100 |
| 250 | 16 | 86 | 98 | 99 | 97 |
| 250 | 32 | 94 | 98 | 100 | 99 |
| 250 | 64 | 100 | 99 | 100 | 100 |
| 250 | 125 | 100 | 100 | 100 | 100 |

*Rates are expressed in g ai/ha for Compound 1 and Compound 15. Data are reported as percent control.
†"Expected" are expected responses calculated according to Colby, S. R. "Calculating Synergistic and Antagonistic Responses of Herbicide Combinations," Weeds, 15(1), pp 20–22 (1967).

The following protocol was used in Table O. Compound numbers are as described on page 28. The data demonstrate the efficacy of the Formula I and Formula IIo mixtures of this invention against specific weeds. The weed control afforded by the mixtures of this invention are not limited, however, to these species.

Test O Protocol

Barnyardgrass (*Echinochloa crus-galli*) and johnsongrass (*Sorghum halepense*) were grown in a greenhouse to the following approximate heights and leaf stages in 10-cm square pots fixed with a mixture of 60% sandy loam soil and 40% MetroMix 350™ growing medium:

| Species | Application | |
|---|---|---|
| | Height (cm) | Leaf Stage |
| *Echinochloa crus-galli* | 9 | 2 |
| *Sorghum halepense* | 10 | 2 |

Treatments were applied to the test species by diluting the compounds in a non-phytotoxic solvent containing a surfactant, and spraying the treatments onto the plants using a stationary laboratory circulating belt sprayer calibrated to deliver 327 L/ha through a single nozzle. Compound 1 was applied at 125, 250 and 500 g ai/ha. Compound 14 was applied at 16, 32, 64 and 125 g ai/ha. Mixtures of Compound 1 at 125, 250 and 500 g ai/ha and Compound 14 at 16, 32, 64 and 125 g ai/ha were also applied. Individual treatments were replicated four times. Treatments were positioned in a greenhouse in a randomized complete block design. The greenhouse was maintained at a 28° C. average daily temperature, and natural light in the greenhouse was supplemented with artificial light to achieve a photoperiod of 14 hours. At 16 days after spraying, the plants were evaluated for injury as compared to control plants that were sprayed only with non-phytotoxic solvent. Injury was evaluated visually using a 0 to 100% scale where 0 indicates no effect and 100 indicates complete control.

Results of Test O are shown in Table O, which lists the observed response of specific weeds to Compound 1 and Compound 15 applied alone as single active ingredients, the observed responses of specific weeds to mixtures of Compound 1 and Compound 15, and the expected additive effect of the herbicidal mixtures of Compound 1 and Compound 15 (Colby's equation). Weeds other than those specifically listed are also controlled by mixtures of Compound 1 and Compound 15. Different ratios of Compound 1 to Compound 15, and different formulation types, also provide useful weed control from the combination of the two herbicides.

TABLE O*

| Effect of Compound 1 and Compound 15 as Active Ingredients Alone and in Mixture | | | | | |
|---|---|---|---|---|---|
| Compound | Compound | Barnyardgrass | | Johnsongrass | |
| 1 | 15 | Mean | Expected† | Mean | Expected |
| Alone | | | | | |
| 125 | 0 | 48 | — | 0 | — |
| 250 | 0 | 70 | — | 0 | — |
| 500 | 0 | 78 | — | 31 | — |
| 0 | 16 | 2 | — | 0 | — |
| 0 | 32 | 2 | — | 0 | — |
| 0 | 64 | 11 | — | 0 | — |
| 0 | 125 | 59 | — | 56 | — |
| Mixtures | | | | | |
| 125 | 16 | 60 | 49 | 2 | 0 |
| 125 | 32 | 75 | 49 | 0 | 0 |
| 125 | 64 | 81 | 54 | 8 | 0 |
| 125 | 125 | 95 | 79 | 39 | 56 |
| 250 | 16 | 81 | 71 | 9 | 0 |
| 250 | 32 | 79 | 71 | 21 | 0 |
| 250 | 64 | 90 | 73 | 49 | 0 |
| 250 | 125 | 96 | 88 | 54 | 56 |
| 500 | 16 | 80 | 78 | 30 | 31 |
| 500 | 32 | 80 | 78 | 55 | 31 |
| 500 | 64 | 88 | 80 | 84 | 31 |
| 500 | 125 | 100 | 91 | 81 | 70 |

*Rates are expressed in g ai/ha for Compound 1 and Compound 15. Data are reported as percent control.
†"Expected" are expected responses calculated according to Colby, S. R. "Calculating Synergistic and Antagonistic Responses of Herbicide Combinations," Weeds, 15(1), pp 20–22 (1967).

The following protocol was used for the test in Table P. Compound numbers are as described on page 28. The data demonstrate the efficacy of the Formula I and Formula IIa mixtures of this invention against specific weeds. The weed control afforded by the mixtures of this invention are not limited, however, to these species.

Test P Protocol

Plastic pots were partially filled with silt loam soil, and seeds of *Cyperus difformis* and *Cyperus iria* were added interspersed in soil to form a 1-cm-thick top layer. The soil was then flooded with water, and the plants grown to the 2-leaf stage for testing. At treatment time, the water level for all plantings was raised to 3 cm above the soil surface. Chemical treatments were formulated in a non-phytotoxic solvent mixture containing a surfactant and applied directly to the paddy water. These treatments were replicated twice. Treated plants and controls were maintained in a greenhouse for 21 days, after which time all species were compared to controls and visually evaluated. Plant response ratings, summarized in Table P are reported on a 0 to 100 scale where 0 is no effect and 100 is complete control.

Results of Test P are shown in Table P, which lists the observed response of specific weeds to Compound 1 and Compound 2 applied alone as single active ingredients, the observed responses of specific weeds to mixtures of Compound 1 and Compound 2, and the expected additive effect of the herbicidal mixtures of Compound 1 and Compound 2 (Colby's equation). Weeds other than those specifically listed are also controlled by mixtures of Compound 1 and Compound 2. Different ratios of Compound 1 to Compound 2, and different formulation types, also provide useful weed control from the combination of the two herbicides.

TABLE P*

| Effect of Compound 1 and Compound 2 as Active Ingredients Alone and in Mixture | | | | | |
|---|---|---|---|---|---|
| Compound | Compound | *Cyperus difformis* | | *Cyperus iria* | |
| 1 | 2 | Mean | Expected† | Mean | Expected |
| Alone | | | | | |
| 25 | 0 | 45 | — | 18 | — |
| 0 | 0.5 | 0 | — | 63 | — |
| 0 | 1.0 | 70 | — | 75 | — |
| Mixtures | | | | | |
| 25 | 0.5 | 70 | 45 | 85 | 74 |
| 25 | 1.0 | 90 | 84 | 85 | 80 |

*Rates are expressed in g ai/ha for Compound 1 and Compound 2. Data are reported as percent control.

TABLE P*-continued

Effect of Compound 1 and Compound 2
as Active Ingredients Alone and in Mixture

| Compound 1 | Compound 2 | Cyperus difformis Mean | Expected† | Cyperus iria Mean | Expected |
|---|---|---|---|---|---|

†"Expected" are expected responses calculated according to Colby, S. R. "Calculating Synergistic and Antagonistic Responses of Herbicide Combinations," Weeds, 15(1), pp 20–22 (1967).

The following protocol was used for the test in Table Q. Compound numbers are as described on page 28. The data demonstrate the efficacy of the Formula I and Formula IIc mixtures of this invention against a specific weed. The weed control afforded by the mixtures of this invention are not limited, however, to this species.

Test O Protocol

Plastic pots were partially filled with silt loam soil, and seeds of *Cyperus iria* were added interspersed in soil to form a 1-cm-thick top layer. The soil was then flooded with water, and the plants grown to the 2-leaf stage for testing. At treatment time, the water level for all plantings was raised to 3 cm above the soil surface. Chemical treatments were formulated in a non-phytotoxic solvent mixture containing a surfactant and applied directly to the paddy water. These treatments were replicated twice. Treated plants and controls were maintained in a greenhouse for 21 days, after which time all species were compared to controls and visually evaluated. Plant response ratings, summarized in Table Q are reported on a 0 to 100 scale where 0 is no effect and 100 is complete control.

Results of Test Q are shown in Table Q, which lists the observed response of a specific weed to Compound 1 and Compound 11 applied alone as single active ingredients, the observed responses of specific weeds to mixtures of Compound 1 and Compound 11, and the expected additive effect of the herbicidal mixtures of Compound 1 and Compound 11 (Colby's equation). Weeds other than those specifically listed are also controlled by mixtures of Compound 1 and Compound 11. Different ratios of Compound 1 to Compound 11, and different formulation types, also provide useful weed control from the combination of the two herbicides.

TABLE Q*

Effect of Compound 1 and Compound 11 as
Active Ingredients Alone and in Mixture

| Compound 1 | Compound 11 | Cyperus iria Mean | Expected† |
|---|---|---|---|
| Alone | | | |
| 50 | 0 | 25 | — |
| 75 | 0 | 55 | — |
| 0 | 0.25 | 0 | — |
| 0 | 0.50 | 0 | — |
| 0 | 0.75 | 20 | — |
| 0 | 1.0 | 60 | — |
| Mixtures | | | |
| 50 | 0.25 | 45 | 25 |
| 50 | 0.50 | 60 | 25 |
| 50 | 0.75 | 75 | 40 |
| 50 | 1.00 | 90 | 70 |
| 75 | 0.25 | 92 | 55 |
| 75 | 0.50 | 100 | 55 |

TABLE Q*-continued

Effect of Compound 1 and Compound 11 as
Active Ingredients Alone and in Mixture

| Compound 1 | Compound 11 | Cyperus iria Mean | Expected† |
|---|---|---|---|
| 75 | 0.75 | 92 | 64 |
| 75 | 1.00 | 85 | 82 |

*Rates are expressed in g ai/ha for Compound 1 and Compound 11. Data are reported as percent control.
†"Expected" are expected responses calculated according to Colby, S. R. "Calculating Synergistic and Antagonistic Responses of Herbicide Combinations," Weeds, 15(1), pp 20–22 (1967).

The following protocol was used for the test in Table R. Compound numbers are as described on page 28. The data demonstrate the efficacy of the Formula I, Formula IIb and Formula IIc mixtures of this invention against a specific weed. The weed control afforded by the mixtures of this invention are not limited, however, to this species.

Test R Protocol

Plastic pots were partially filled with silt loam soil, and seeds of ducksalad (*Heteranthera limosa*) were added interspersed in soil to form a 1-cm-thick top layer. The soil was then flooded with water, and the plants grown to the 2-leaf stage for testing. At treatment time, the water level for all plantings was raised to 3 cm above the soil surface. Chemical treatments were formulated in a non-phytotoxic solvent mixture containing a surfactant and applied directly to the paddy water. These treatments were replicated twice. Treated plants and controls were maintained in a greenhouse for 21 days, after which time all species were compared to controls and visually evaluated. Plant response ratings, summarized in Table R are reported on a 0 to 100 scale where 0 is no effect and 100 is complete control.

Results of Test R are shown in Table R, which lists the observed response of a specific weed to Compound 1 as a single active ingredient and Compound 3 and Compound 11 mixed together without Compound 1, the observed responses of specific weeds to mixtures of Compound 1 with the mixture of Compound 3 and Compound 11, and the expected additive effect of the herbicidal mixtures of Compound 1 with the mixture of Compound 3 and Compound 11 (Colby's equation). Weeds other than those specifically listed are also controlled by mixtures of Compound 1 with Compound 3 and Compound 11. Different ratios of Compound 1 to Compound 3 to Compound 11, and different formulation types, also provide useful weed control from the combination of the three herbicides.

TABLE R*

Effect of Compound 1, Compound 3 and Compound 11
as Active Ingredients Alone and in Mixture

| Compound 1 | Compound 3 | Compound 11 | Ducksalad Mean | Expected† |
|---|---|---|---|---|
| 75 | 0 | 0 | 0 | — |
| 0 | 0.125 | 0.125 | 0 | — |
| 0 | 0.25 | 0.25 | 10 | — |
| 0 | 0.375 | 0.375 | 50 | — |
| 0 | 0.50 | 0.50 | 95 | — |
| 0 | 1.00 | 1.00 | 100 | — |
| Mixtures with Compound 1 | | | | |
| 75 | 0.125 | 0.125 | 18 | 0 |

TABLE R*-continued

Effect of Compound 1, Compound 3 and Compound 11
as Active Ingredients Alone and in Mixture

| Compound 1 | Compound 3 | Compound 11 | Ducksalad Mean | Expected† |
|---|---|---|---|---|
| 75 | 0.25 | 0.25 | 35 | 10 |
| 75 | 0.375 | 0.375 | 86 | 50 |
| 75 | 0.50 | 0.50 | 100 | 95 |
| 75 | 1.00 | 1.00 | 100 | 100 |

*Rates are expressed in g ai/ha for Compound 1, Compound 3 and Compound 11. Data are reported as percent control.
†"Expected" are expected responses calculated according to Colby, S. R. "Calculating Synergistic and Antagonistic Responses of Herbicide Combinations," Weeds, 15(1), pp 20–22 (1967).

The following protocol was used for the test in Table S. Compound numbers are as described on page 28. The data demonstrate the efficacy of the Formula I, Formula IIb and Formula IId mixtures of this invention against a specific weed. The weed control afforded by the mixtures of this invention are not limited, however, to this species.

Test S Protocol

Plastic pots were partially filled with silt loam soil, and seeds of ducksalad (*Heteranthera limosa*) were added interspersed in soil to form a 1-cm-thick top layer. The soil was then flooded with water, and the plants grown to the 2-leaf stage for testing. At treatment time, the water level for all plantings was raised to 3 cm above the soil surface. Chemical treatments were formulated in a non-phytotoxic solvent mixture containing a surfactant and applied directly to the paddy water. These treatments were replicated twice. Treated plants and controls were maintained in a greenhouse for 21 days, after which time all species were compared to controls and visually evaluated. Plant response ratings, summarized in Table S are reported on a 0 to 100 scale where 0 is no effect and 100 is complete control.

Results of Test S are shown in Table S, which lists the observed response of a specific weed to Compound 1 as a single active ingredient and Compound 3 and Compound 16 mixed together without Compound 1, the observed responses of specific weeds to mixtures of Compound 1 with the mixture of Compound 3 and Compound 16, and the expected additive effect of the herbicidal mixtures of Compound 1 with the mixture of Compound 3 and Compound 16 (Colby's equation). Weeds other than those specifically listed are also controlled by mixtures of Compound 1 with Compound 3 and Compound 16. Different ratios of Compound 1 to Compound 3 to Compound 16, and different formulation types, also provide useful weed control from the combination of the three herbicides.

TABLE S*

Effect of Compound 1, Compound 3 and Compound 16
as Active Ingredients Alone and in Mixture

| Compound 1 | Compound 3 | Compound 16 | Ducksalad Mean | Expected† |
|---|---|---|---|---|
| 50 | 0 | 0 | 0 | — |
| 75 | 0 | 0 | 0 | — |
| 0 | 0.17 | 0.83 | 20 | — |
| 0 | 0.33 | 1.67 | 70 | — |
| 0 | 0.50 | 2.50 | 95 | — |
| 0 | 0.67 | 3.33 | 100 | — |

TABLE S*-continued

Effect of Compound 1, Compound 3 and Compound 16
as Active Ingredients Alone and in Mixture

| Compound 1 | Compound 3 | Compound 16 | Ducksalad Mean | Expected† |
|---|---|---|---|---|
| Mixtures with Compound 1 | | | | |
| 50 | 0.17 | 0.83 | 25 | 20 |
| 50 | 0.33 | 1.67 | 82 | 70 |
| 50 | 0.50 | 2.50 | 95 | 95 |
| 50 | 0.67 | 3.33 | 100 | 100 |
| 75 | 0.17 | 0.83 | 55 | 20 |
| 75 | 0.33 | 1.67 | 82 | 70 |
| 75 | 0.50 | 2.50 | 100 | 95 |
| 75 | 0.67 | 3.33 | 100 | 100 |

*Rates are expressed in g ai/ha for Compound 1, Compound 3 and Compound 16. Data are reported as percent control.
†"Expected" are expected responses calculated according to Colby, S. R. "Calculating Synergistic and Antagonistic Responses of Herbicide Combinations," Weeds, 15(1), pp 20–22 (1967).

The following protocol was used for the test in Table T. Compound numbers are as described on page 28. The data demonstrate the efficacy of the Formula I, Formula IIb and Formula IId mixtures of this invention against a specific weed. The weed control afforded by the mixtures of this invention are not limited, however, to this species.

Test T Protocol

Herbicides were applied to weeds and transplanted rice in outdoor flooded field plots measuring 3-by-5 meters at an application timing of 5 days after transplanting 21-day-old Indica IR64 rice seedlings. At the time of application, *Monochoria vaginalis* was in the early preemergence stage of growth. Water depth at application was 4–6 cm and was maintained on the plots for at least 2 weeks after treatment. Compound 1 was formulated as a 30% emulsifiable concentrate, and the 1:5 mixture of Compound 3 and Compound 16 was formulated as a 10% wettable powder. The herbicides were applied using a knapsack sprayer with a single fan nozzle delivering a spray volume of 300 liters/ha. At 28 days after application, weed control was calculated quantitatively on a 0 to 100 percent scale, where 0 is no effect and 100 is complete control, by comparing weed density in treated versus untreated plots. Each table entry is a mean of three replications.

Results of Test T are shown in Table T, which lists the observed response of a specific weed to Compound 1 as a single active ingredient and Compound 3 and Compound 16 mixed together without Compound 1, the observed responses of specific weeds to mixtures of Compound 1 with the mixture of Compound 3 and Compound 16, and the expected additive effect of the herbicidal mixtures of Compound 1 with the mixture of Compound 3 and Compound 16 (Colby's equation). Weeds other than those specifically listed are also controlled by mixtures of Compound 1 with Compound 3 and Compound 16. Different ratios of Compound 1 to Compound 3 to Compound 16, and different formulation types, also provide useful weed control from the combination of the three herbicides.

TABLE T*

Effect of Compound 1 Compound 3 and Compound 16 as Active Ingredients Alone and in Mixture

| Compound 1 | Compound 3 | Compound 16 | Monochoria vaginalis Mean | Expected† |
|---|---|---|---|---|
| 200 | 0 | 0 | 16 | — |
| 300 | 0 | 0 | 34 | — |
| 0 | 0.67 | 3.33 | 26 | — |
| 0 | 1.33 | 6.67 | 74 | |
| 0 | 2.50 | 12.50 | 100 | |
| Mixtures with Compound 1 | | | | |
| 200 | 0.67 | 3.33 | 88 | 38 |
| 200 | 1.33 | 6.67 | 95 | 78 |
| 200 | 2.50 | 12.50 | 100 | 100 |
| 300 | 0.67 | 3.33 | 80 | 51 |
| 300 | 1.33 | 6.67 | 98 | 83 |
| 300 | 2.50 | 12.50 | 100 | 100 |

*Rates are expressed in g ai/ha for Compound 1, Compound 3 and Compound 16. Data are reported as percent control.
†"Expected" are expected responses calculated according to Colby, S. R. "Calculating Synergistic and Antagonistic Responses of Herbicide Combinations," Weeds, 15(1), pp 20–22 (1967).

What is claimed is:

1. A herbicidally effective mixture of anilofos (Formula I) with propanil (Formula IIn).

2. An agriculturally suitable composition for controlling the growth of undesired vegetation comprising an effective amount of the mixture of claim 1 and at least one of the following: surfactant, solid or liquid diluent.

3. A method for controlling the growth of undesired vegetation by applying to the locus of the undesired vegetation a herbicidally effective amount of the mixture of claim 1.

4. A method for controlling the growth of undesired vegetation by applying to the locus of the undesired vegetation a herbicidally effective amount of the mixture of claim 1.

* * * * *

UNITED STATES PATENT AND TRADEMARK OFFICE
CERTIFICATE OF CORRECTION

PATENT NO. : 5,736,486
DATED : April 7, 1998
INVENTOR(S) : Pappas-Fader et al.

It is certified that error appears in the above-identified patent and that said Letters Patent is hereby corrected as shown below:

Column 58, claim 4, delete "the undesired vegetation" and substitute therefore "a rice crop".

Signed and Sealed this

Eighth Day of December, 1998

Attest:

BRUCE LEHMAN

*Attesting Officer*  *Commissioner of Patents and Trademarks*